United States Patent
Thran et al.

(10) Patent No.: US 8,693,621 B2
(45) Date of Patent: Apr. 8, 2014

(54) SOURCE AND/OR DETECTOR POSITIONING SYSTEM

(75) Inventors: Axel Thran, Hamburg (DE); Claas Bontus, Hamburg (DE); Peter Forthmann, Sandesneben (DE); Roland Proksa, Hamburg (DE); Ronald B. Sharpless, Cleveland, OH (US); Dominic J. Heuscher, Aurora, OH (US); Felix Peeters, Heide (NL); Johannes Bathazar Maria Soetens, Esbeek (NL)

(73) Assignee: Koninklijke Philips N. V., Eindhoven (NL)

( * ) Notice: Subject to any disclaimer, the term of this patent is extended or adjusted under 35 U.S.C. 154(b) by 682 days.

(21) Appl. No.: 12/990,278

(22) PCT Filed: Apr. 30, 2009

(86) PCT No.: PCT/IB2009/051764
§ 371 (c)(1),
(2), (4) Date: Oct. 29, 2010

(87) PCT Pub. No.: WO2009/133530
PCT Pub. Date: Nov. 5, 2009

(65) Prior Publication Data
US 2011/0058644 A1 Mar. 10, 2011

Related U.S. Application Data

(60) Provisional application No. 61/101,159, filed on Sep. 30, 2008, provisional application No. 61/049,441, filed on May 1, 2008.

(51) Int. Cl.
*A61B 6/03* (2006.01)

(52) U.S. Cl.
USPC .......................................................... 378/17

(58) Field of Classification Search
USPC .......................................................... 378/17
See application file for complete search history.

(56) References Cited

U.S. PATENT DOCUMENTS

| 4,045,672 | A | 8/1977 | Watanabe |
| 4,093,863 | A | 6/1978 | Zacher, Jr. |
| 4,112,303 | A | 9/1978 | Brandt |
| 4,817,119 | A | 3/1989 | Ledley et al. |

(Continued)

FOREIGN PATENT DOCUMENTS

| WO | WO2004/023123 | * | 3/2004 | ............. G01N 23/04 |
| WO | 2008024585 A1 | | 2/2008 | |
| WO | 2008026153 A2 | | 3/2008 | |
| WO | 2008042564 A1 | | 4/2008 | |

*Primary Examiner* — Allen C. Ho

(57) ABSTRACT

A medical imaging system includes a generally stationary gantry (102) and a rotating gantry (106), rotatably supported by the generally stationary gantry (102), that rotates about a longitudinal axis around an examination region. The medical imaging system further includes a radiation source (112) that emits a radiation beam that traverses the examination region. The radiation source (112) is moveably affixed to the rotating gantry (106) so as to translate in a direction of the longitudinal axis with respect to the rotating gantry (106) while scanning a subject in the examination region. The medical imaging system further includes a detector array (120) that detects the radiation beam that traverses the examination region and generates a signal indicative thereof. The detector array (120) is moveably affixed to the rotating gantry (106) so as to move in coordination with the radiation source (112) while scanning the subject in the examination region.

44 Claims, 19 Drawing Sheets

(56) References Cited

U.S. PATENT DOCUMENTS

| | | | |
|---|---|---|---|
| 5,448,607 A | 9/1995 | McKenna | |
| 5,909,477 A | 6/1999 | Crawford et al. | |
| 5,949,843 A | 9/1999 | Tamaki et al. | |
| 6,400,791 B1 | 6/2002 | Schwarz | |
| 6,580,777 B1 * | 6/2003 | Ueki et al. | 378/17 |
| 6,683,935 B2 * | 1/2004 | Moore | 378/17 |
| 6,704,392 B2 | 3/2004 | Ebben et al. | |
| 6,751,283 B2 | 6/2004 | van de Haar | |
| 6,760,399 B2 | 7/2004 | Malamud | |
| 6,862,337 B2 | 3/2005 | Claus et al. | |
| 7,108,421 B2 * | 9/2006 | Gregerson et al. | 378/197 |
| 7,235,790 B2 * | 6/2007 | Hoge | 250/370.11 |
| 7,236,560 B2 * | 6/2007 | Malamud | 378/7 |
| 7,248,666 B2 | 7/2007 | Kasuya | |
| 7,338,207 B2 | 3/2008 | Gregerson et al. | |
| 7,418,074 B2 | 8/2008 | Du | |
| 7,453,978 B1 | 11/2008 | DiBianca et al. | |
| 7,548,604 B2 * | 6/2009 | De Man et al. | 378/17 |
| 7,940,887 B2 * | 5/2011 | Shibata et al. | 378/21 |
| 8,213,567 B2 * | 7/2012 | Sakai | 378/10 |
| 8,401,144 B2 * | 3/2013 | Forthmann et al. | 378/19 |
| 8,462,911 B2 * | 6/2013 | Vesel et al. | 378/9 |
| 8,520,974 B2 * | 8/2013 | Fujita et al. | 382/275 |
| 8,571,172 B2 * | 10/2013 | Dafni et al. | 378/8 |
| 2003/0035513 A1 | 2/2003 | Horiuchi | |
| 2004/0013225 A1 | 1/2004 | Gregerson et al. | |
| 2004/0028173 A1 | 2/2004 | van de Haar | |
| 2005/0100126 A1 | 5/2005 | Mistretta et al. | |
| 2008/0031403 A1 | 2/2008 | Harer et al. | |

* cited by examiner

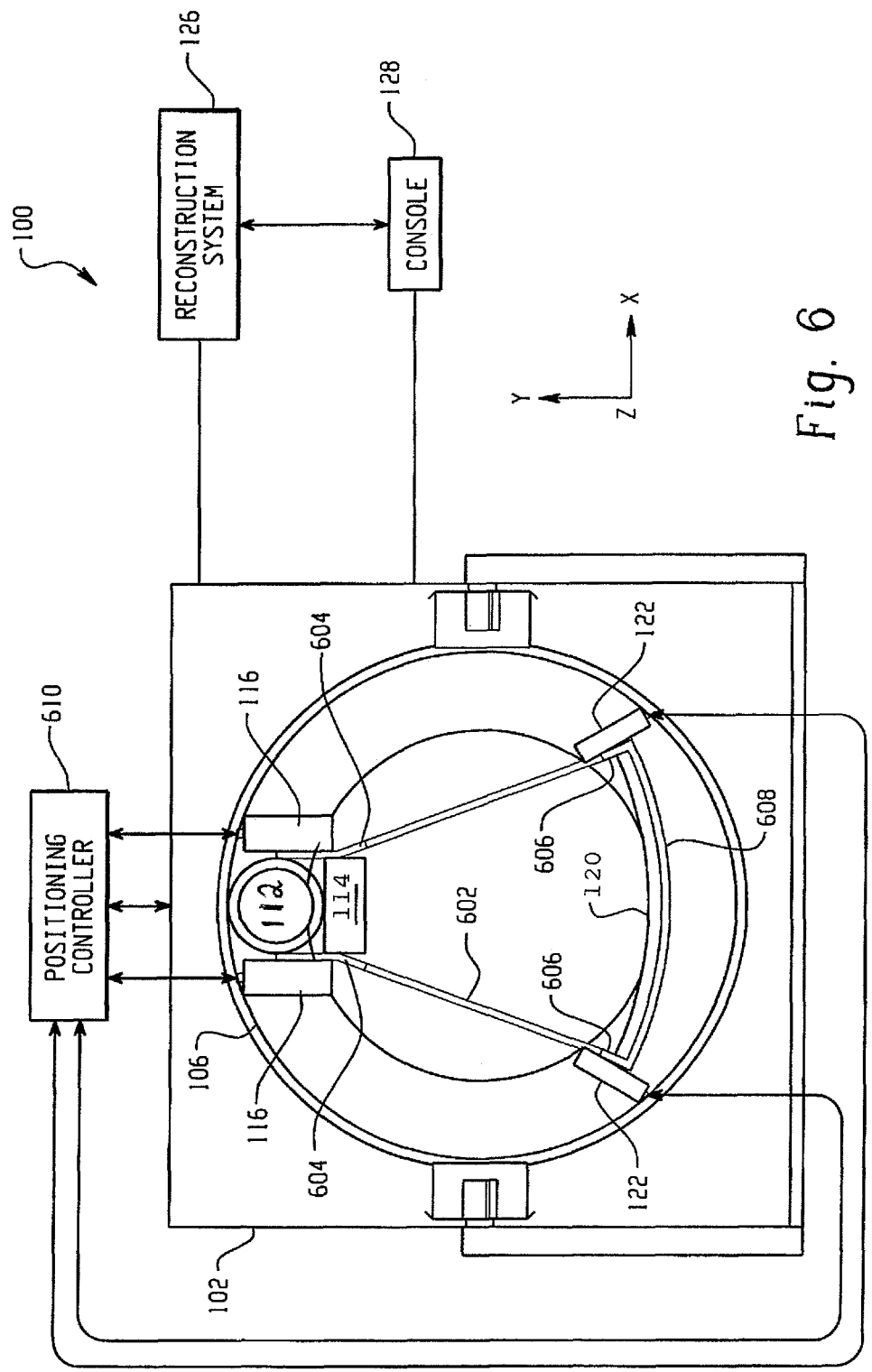

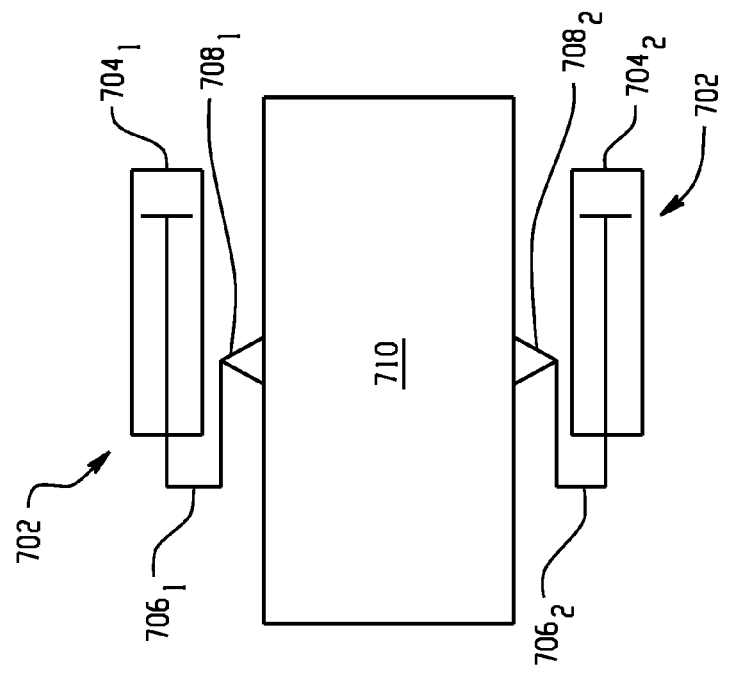
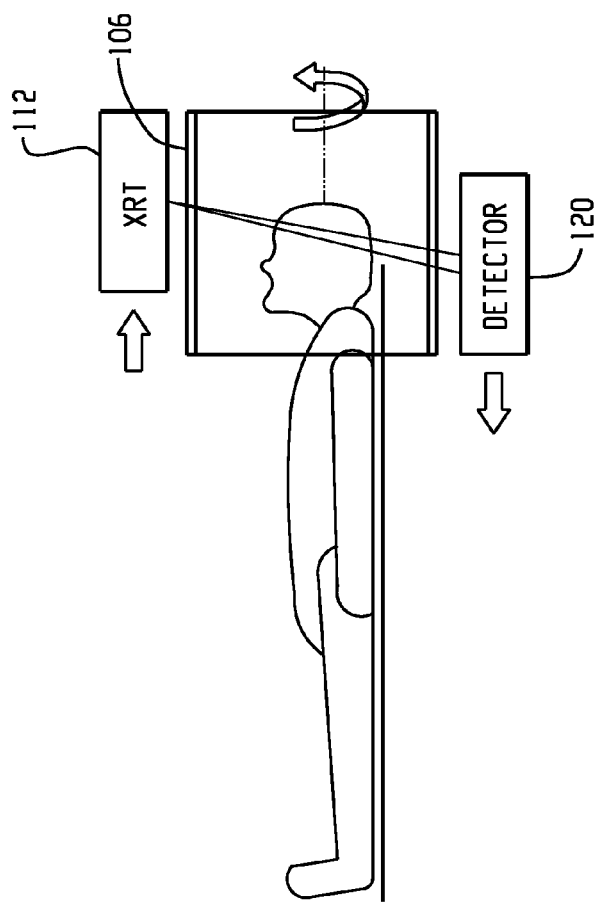
Fig. 7b
Fig. 7a

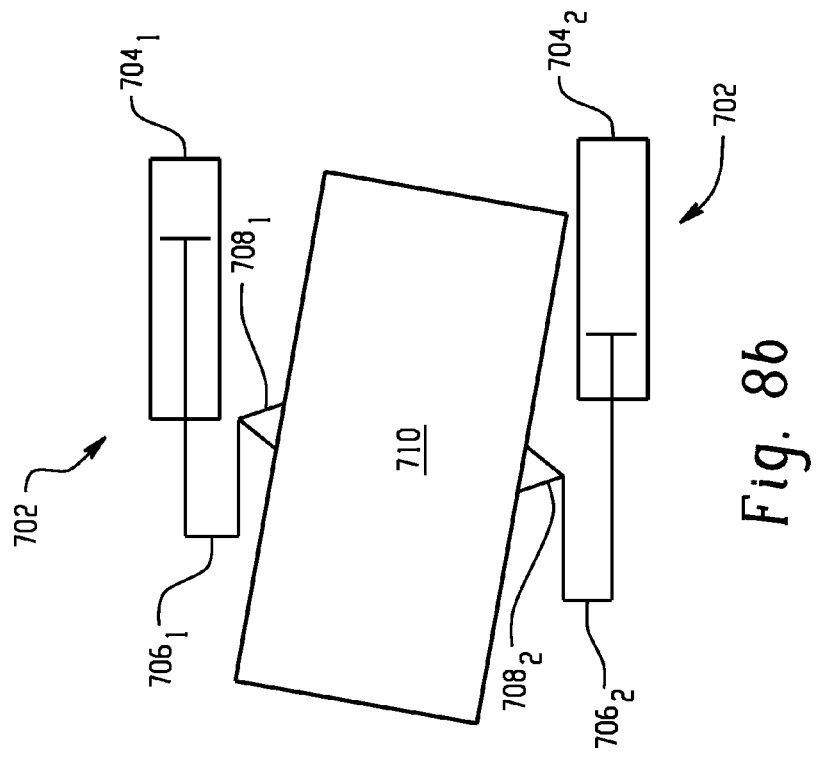
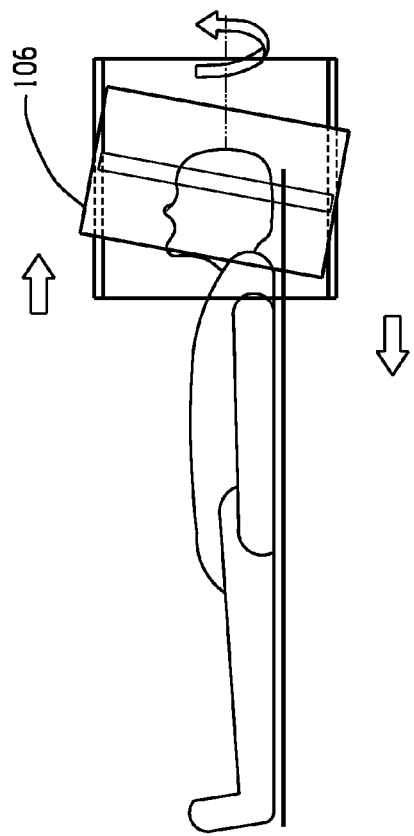
Fig. 8a
Fig. 8b

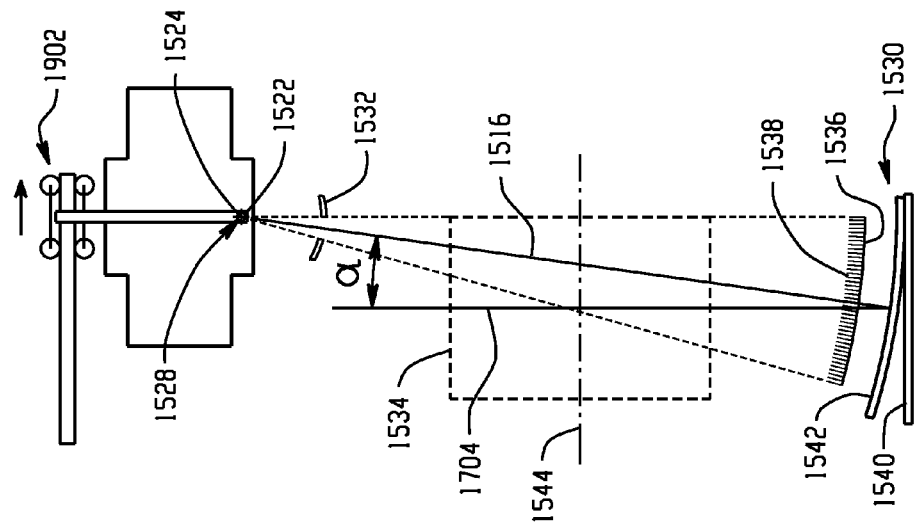
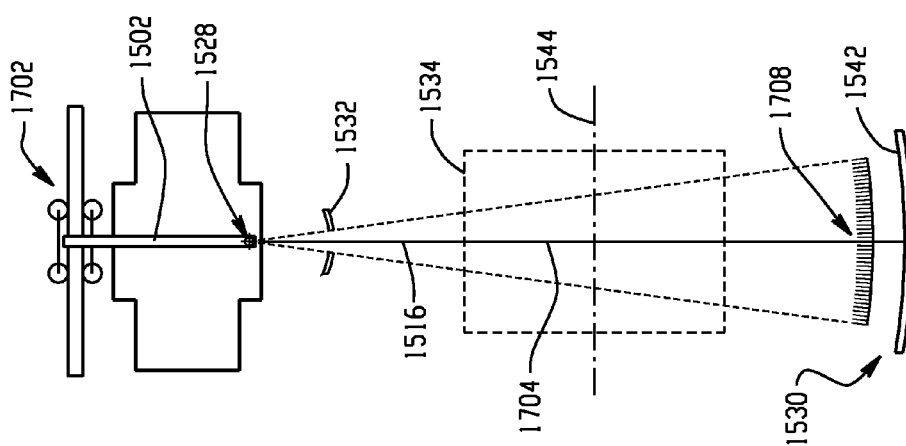
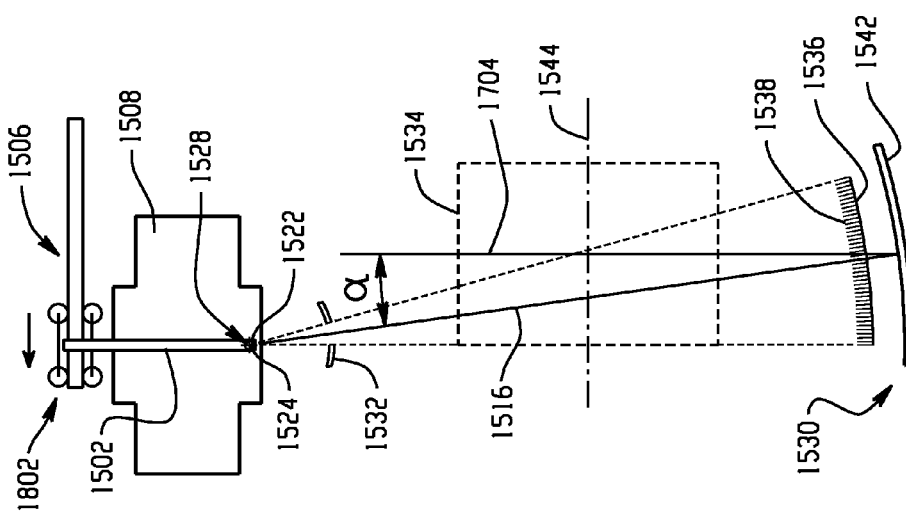

SOURCE AND/OR DETECTOR POSITIONING SYSTEM

CROSS REFERENCE TO RELATED APPLICATIONS

This application claims the benefit of U.S. provisional application Ser. No. 61/049,441 filed May 1, 2008 and U.S. provisional Ser. No. 61/101,159 filed Sep. 30, 2008, both of which are incorporated herein by reference.

DESCRIPTION

The following generally relates to positioning a radiation source and/or a radiation sensitive detector array in a longitudinal direction during an imaging procedure and finds particular application to computed tomography (CT). However, it also amenable to other medical imaging applications and to non-medical imaging applications.

A computed tomography (CT) scanner generally includes an x-ray tube and a detector array that detects radiation emitted from the x-ray tube. The x-ray tube and the detector array are affixed on a rotor on opposite side of an examination region. The rotor is rotatably supported by a stationary frame and rotates about a longitudinal axis, around the examination region, thereby rotating the x-ray tube and a detector array around the examination region. A patient support supports an object in the examination region.

The stationary frame is stationary in that it generally remains in a vertical position during scanning. However, conventional systems have included stationary frames configured to tilt up to ±30 degrees in a direction of the longitudinal axis. Tilting the stationary gantry tilts the x-ray tube and the detector array, which causes the x-ray beam to traverse the examination region from an acute angle. The stationary gantry has been tilted for various reasons such as to achieve a particular radiation source trajectory such as elliptical trajectory and to avoid exposing radiation sensitive anatomy, such as the optical nerves, while scanning the inner ear.

Unfortunately, in order to tilt the gantry, the scanner requires a tilt support and control system that can support and accurately position the large mass of the gantry. Such a system may increase overall system cost and/or the footprint of the scanner, consume the relatively limited space within the stationary gantry, and add substantial weight to the scanner. Furthermore, tilt collision avoidance algorithms are needed to mitigate pinch points, or points of potential contact between the stationary frame and a patient. Moreover, tilting the stationary gantry reduces the effective aperture size of the examination region, which may require the clinician to reposition the patient within the examination region.

Aspects herein address the above-referenced matters and/or others.

According to one aspect, a medical imaging system includes a generally stationary gantry and a rotating gantry, rotatably supported by the generally stationary gantry, that rotates about a longitudinal axis around an examination region. The medical imaging system further includes a radiation source that emits a radiation beam that traverses the examination region. The radiation source is moveably affixed to the rotating gantry so as to translate in a direction of the longitudinal axis with respect to the rotating gantry while scanning a subject in the examination region. The medical imaging system further includes a detector array that detects the radiation beam that traverses the examination region and generates a signal indicative thereof. The detector array is moveably affixed to the rotating gantry so as to move in coordination with the radiation source while scanning the subject in the examination region.

According to another aspect, a method includes rotating a rotating gantry rotatably coupled to a stationary gantry about a longitudinal axis around an examination region, and translating a radiation source and a detector array, which are coupled to and rotate with the rotating gantry, in a direction of the longitudinal axis with respect to the stationary gantry during scanning.

According to another aspect, a medical imaging system includes means for rotating a rotating gantry rotatably supported by a stationary gantry about a longitudinal axis around an examination region, wherein the rotating gantry emits radiation that traverses the examination region, means for moving a radiation source, which is coupled to and rotates with the rotating gantry, in a direction of the longitudinal axis with respect to the stationary gantry during scanning to so that the radiation beam traverses the examination region at a tilt angle, means for detecting the emitted radiation with a detector array that is coupled to and rotates with the rotating gantry, and means for generating image data indicative of the detected radiation.

In another aspect, a computed tomography (CT) scanner includes a generally stationary gantry, a rotating gantry, rotatably supported by the generally stationary gantry, that rotates about a longitudinal axis around an examination region; a radiation source that emits radiation beam; a source collimator with a least one moveable radiation collimating plate that collimates the radiation emitted by the source to produce a radiation beam that traverses the examination region; a detector array that detects the radiation beam that traverses the examination region and generates a signal indicative thereof; an anti-scatter grid disposed between the examination region and the detector array; and a reconstructor that reconstructs the signal from the detector array to generated volumetric image data indicative of the examination region; wherein the radiation source and the detector array translate along the longitudinal axis in coordination to create an effective tilt without tilting the stationary gantry.

According to another aspect, an imaging system includes a rotating gantry that rotates about a longitudinal axis around the examination region. A radiation source includes a focal spot that emits radiation that traverses an examination region. The radiation source is moveably affixed to the rotating gantry and translates in a direction of the longitudinal axis. A detector array is focused at the focal spot. The detector array rolls in coordination with the translation of radiation source, thereby maintaining the focus between the detector array and the focal spot.

According to another aspect, a method includes translating a focal spot of a radiation source in a direction of a z-axis and concurrently rolling a detector array focused at the focal spot in coordination with the translation of the focal spot so as to maintain a focus between the detector array and the focal spot as the focal spot translates.

The invention may take form in various components and arrangements of components, and in various steps and arrangements of steps. The drawings are only for purposes of illustrating the preferred embodiments and are not to be construed as limiting the invention.

FIG. 6 illustrates an example in which the source/collimator and detector array are physically coupled together.

FIGS. 7a, 7b, 8a, 8b, 9a and 9b illustrate an example in which the source/collimator and detector array translate and rotate in a direction of the longitudinal axis.

FIGS. 15-19 illustrate an embodiment in which the radiation source translates and the detector array rolls in coordination with the radiation source.

The following general relates to a computed tomography (CT) scanner in which the x-ray tube, the source collimator, and/or the detector array translate along the z-axis and/or tilt in a direction of the z-axis independent of and/or with each other and/or the stationary gantry/frame. It is to be appreciated that such movement may occur before, during and/or after a scan. In one instance, by dynamically moving one or more of the x-ray tube, the source collimator, or the detector array during a scan, a tilt angle is achieved without tilting the stationary gantry/frame, although the stationary gantry/frame can also be tilted.

Figure 1:
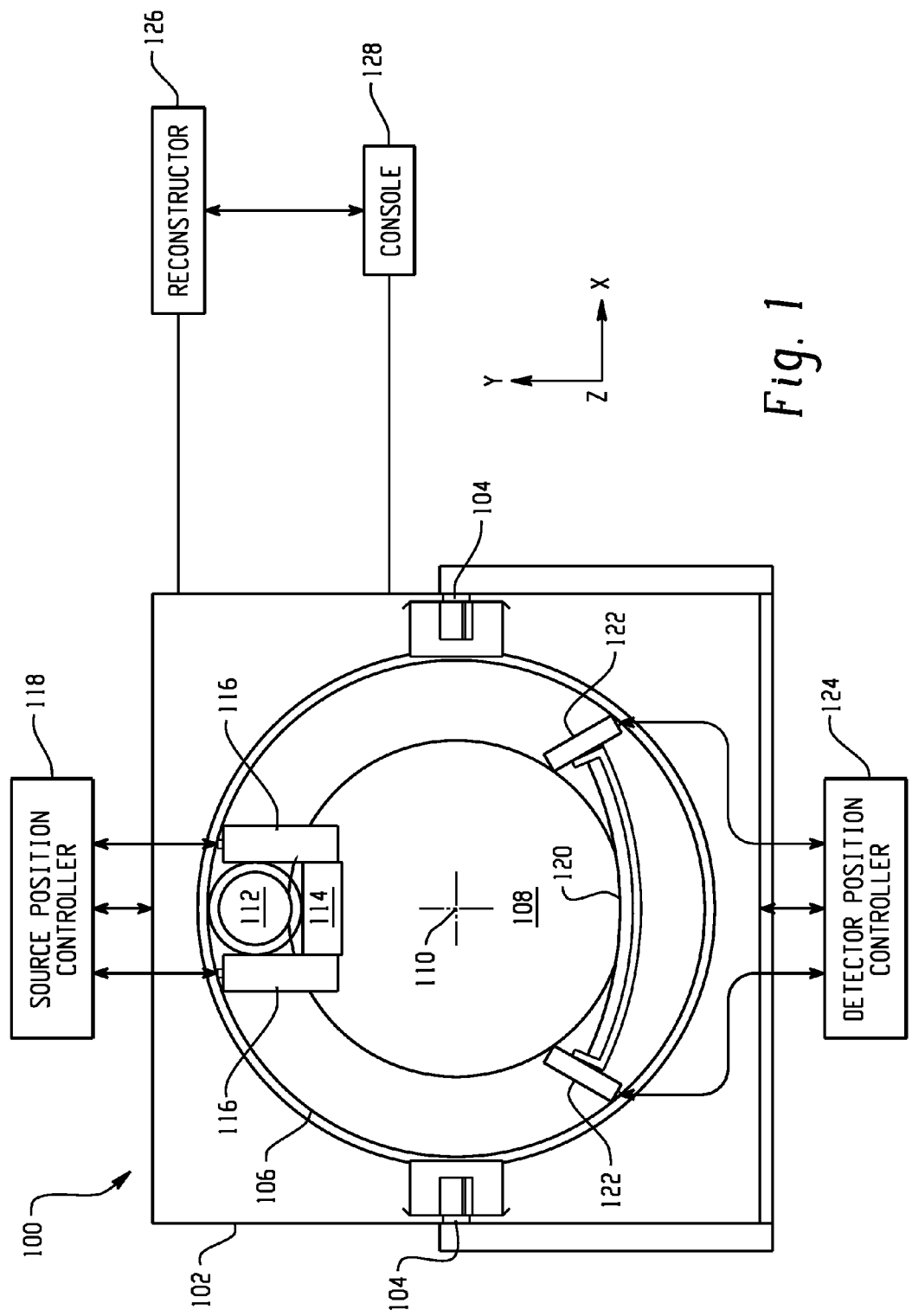
FIG. 1 illustrates an imaging system including a source/collimator and a detector array positioning system.

Initially referring to FIG. 1, a CT scanner 100 includes a stationary gantry portion or frame 102, which is stationary in the sense that it is generally stationary during scanning. However, the stationary gantry 102 may be configured to tilt about tilt axes 104 and/or otherwise move. The scanner 100 also includes a rotating gantry portion or rotor 106, which is rotatably supported by the stationary gantry 102. The rotating gantry 106 rotates around an examination region 108 about a longitudinal or z-axis 110.

A radiation source 112, such as a cylinder tube or other x-ray tube, emits radiation that traverses the examination region 108. A source collimator 114 collimates the emitted radiation so that a generally conical, fan, wedge, or other shaped radiation beam traverses the examination region 108. The radiation source 112 and/or the source collimator 114 are supported by and both rotate with the rotating gantry 106 around the examination region 108. The radiation source 112 and the source collimator 114 are moveably affixed to the rotating gantry 106 through a bearing or the like, as described in greater detail below. In the illustrated example, the radiation source 112 and the source collimator 114 are mechanically coupled together. As such, the radiation source 112 and the source collimator 114 are also referred to herein as the source/collimator 112/114.

A source positioning system 116 selectively moves the source/collimator 112/114 to suitably position the source/collimator 112/114 before, during, and/or after a scan. As shown, the scanner 100 includes two source positioning systems 116, one on each side of the source/collimator 112/114. However, in another embodiment, the scanner 100 includes one or more than two source positioning systems 116. A source position controller 118 communicates with the source positioning system 116 and generates a signal indicative of a desired movement of the radiation source/collimator 112/114. As described in greater detail below, such movement may include a translational movement of the radiation source/collimator 112/114 in the direction of the longitudinal axis 110 and/or a rotational movement of the radiation source/collimator 112/114 in the direction of the longitudinal axis 110.

A detector array 120 is located across from the source 112, opposite the examination region 108. The detector array 120 includes one or more rows of radiation sensitive pixels that extend along a transverse direction. The radiation sensitive pixels detect radiation traversing the examination region 108 and respectively generate a signal indicative thereof. Similar to the source 112 and the collimator 114, the illustrated detector array 120 is supported by and rotates with the rotating gantry 106 around the examination region 108. The detector array 120 is moveably affixed to the rotating gantry 106 through a bearing and/or pivot, as described in greater detail below.

When the detector array 120 is configured to translate and/or rotate, a detector positioning system 122 selectively moves the detector array 120 to suitably position the detector array 120 before, during, and/or after a scan. As shown, the scanner 100 includes two detector array positioning systems 122, one on each side of the detector array 120. However, similar to the source positioning system 116, in another embodiment there is one or more than two detector positioning systems 122. A detector position controller 124 communicates with the detector positioning system 122 and generates a signal indicative of the movement of the detector array 120. It is to be appreciated that such movement may be in coordination with or independent from movement of the source/collimator 112/114, including in a same direction and in an opposite direction. With the detector array 120 configured to pivot, the detector array 120 pivots when the source/collimator 112/114 translates. An anti-scatter grid (not shown) may be used in connection with the detector array 120.

A reconstructor 126 reconstructs the signals generated by the detector array 120 and generates volumetric image data indicative of the examination region 108. A patient support (not shown), such as a couch, supports a patient in the examination region 108. The patient support is movable along an x, y and/or z-axis in coordination with the rotation of the rotating gantry 106 to facilitate achieving elliptical, helical, axial, and/or other desired scanning trajectories. A general purpose computing system serves as an operator console 128, which includes input and human readable output devices such as a keyboard and/or mouse and a display and/or printer. Software resident on the computing system controls operation of the system 100, for example, by sending positioning instructions for the source/collimator 112/114 and/or the detector array 120 based on a user selected scan protocol and/or otherwise.

Through selectively moving the source/collimator 112/114 and/or the detector array 120 as described herein with respect to each other, various tilt trajectories such as an elliptical trajectory are achieved without having to tilt the stationary gantry 102. Thus, the scanner 100 can be configured so that the stationary gantry 102 does not tilt. In one instance, this may mitigate one or more of the aforementioned disadvantages of tilting the stationary gantry 102. By way of example, moving the source/collimator 112/114 and/or the detector array 120 as such instead of tilting the stationary gantry 102 may mitigate potential collisions between the stationary gantry 102 and one or more objects such as medical equipment in the examination room and/or a patient being scanned. In addition, eliminating the mechanism used to tilt the stationary gantry 102 may reduce overall scanner weight, size, and/or cost. Of course, tilt trajectories can still be achieved when the stationary gantry 102 is configured to tilt, with or without tilting the stationary gantry 102. It is also to be understood that a particular scan protocol may call for movement of one of the source/collimator 112/114, the detector array 120, or the stationary gantry 102, or two or more of the source/collimator 112/114, the detector array 120, or the stationary gantry 102.

Figure 2:
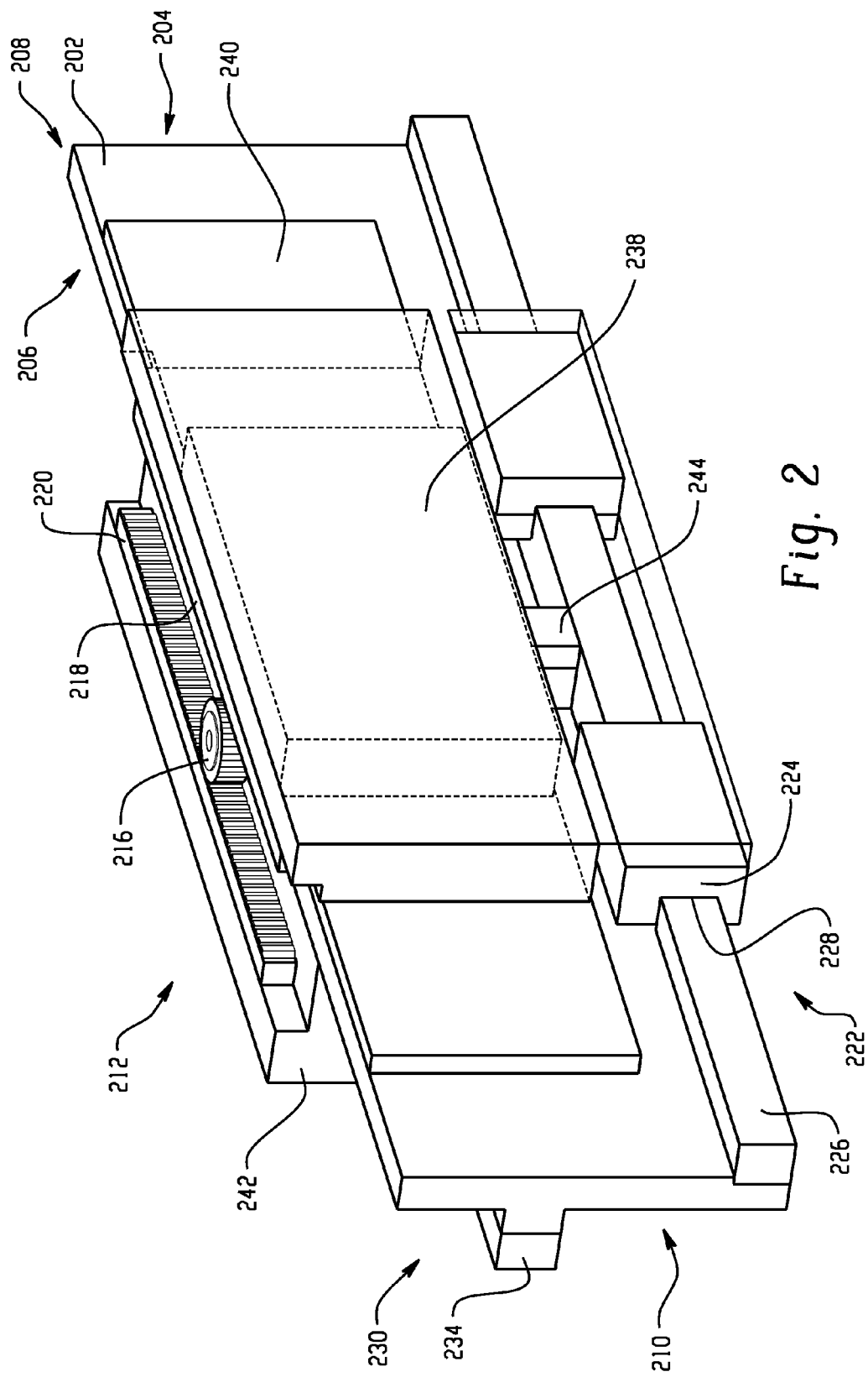
FIGS. 2 and 3 illustrate an example source/collimator positioning system.
Figure 3:
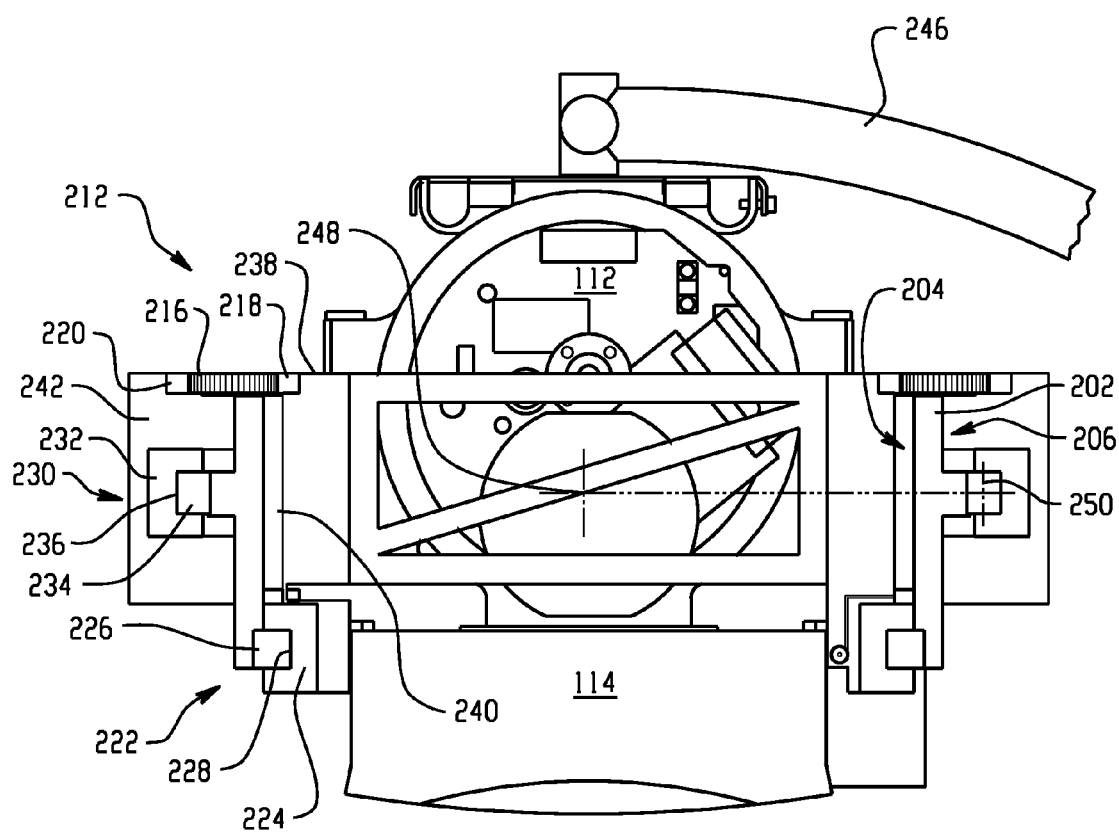

FIGS. 2 and 3 illustrate an example source positioning system 116. In the illustrated example, the source positioning system 116 includes an elongate frame portion 202, which is positioned next to the source/collimator 112/114 along a transverse axis and extends in a direction of the longitudinal axis 110. The frame portion 202 includes a first major or inner side 204, which faces the source/collimator 112/114, and a second major opposing or outer side 206, which faces away from the source/collimator 112/114. The elongate frame portion 202 also includes first and second opposing ends 208 and 210. The end 208 is fastened to the rotating gantry 106 through a fastening mechanism such as a bolt, a screw, a rivet, an adhesive, a bond, etc., which affixes the frame portion 202 to the rotating gantry 106. In another embodiment, the frame portion 202 is magnetically coupled to the rotating gantry 106. In yet another embodiment, the frame portion 202 and the rotating gantry 106 are a single unitary structure.

The source positioning system 116 further includes a first bearing 212 affixed to the frame portion 202. The illustrated first bearing 212 is a rack and pinion type bearing. However, other bearings such as spear gear, a chain, a belt, etc. can alternatively be used. The first bearing 212 includes gears 216, 218 and 220. The pinion 216 is a generally circular gear that includes a plurality teeth, and each of the racks 218 and 220 is a generally flat gear that includes a plurality of teeth, which are complementary to the teeth of the pinion 216. The racks 218 and 220 are located on opposite sides of the frame portion 202, with the rack 218 being by the inner side 204 and the rack 220 being by the outer side 206.

The gears 216-220 are arranged with respect to each other such that movement of any one of the gears 216-220 causes the teeth of the gears 216 and 218 to engage and the teeth of the gears 216 and 220 to engage, which results in motion all three of the gears 216-220. In the illustrate example, a translational motion of one of the rack 218 (or 220) in one direction causes rotational motion of the pinion 216, which causes translational motion of the other rack 220 (or 218) in an opposing direction relative to the rack 218 (or 220). The first bearing 212 is affixed to the frame so that the gears 218 and 220 translate in a direction of the longitudinal axis 110.

A second bearing 222 of the source positioning system 116 includes a linear bearing. However, the second bearing 222 can alternatively include a chain, a belt, a lead screw, a ball screw, etc. The second bearing 222 includes a slide 224 and a rail 226. The slide 224 includes a groove 228. The rail 226 extends a substantial length of the frame portion 202, is affixed to the inner side 204 of the frame portion 202, and is disposed in the groove 228. The slide 224 is generally free to slide or translates along the rail 226. The bearing 222 is affixed to the frame and configured so that the slide 224 translates in the longitudinal direction.

A third bearing 230 of the source positioning system 116 also includes a linear bearing and can be another type of bearing such as those noted above. The third bearing 230 includes a slide 232 and a rail 234. The slide 232 includes a grove 236. The rail 234 extends a substantial length of the frame portion 202, is affixed to the outer side 206 of the frame portion 202, and is disposed in the groove 236. The slide 232 is generally free to slide or translates along the rail 234. The bearing 230 is affixed to the frame and configured so that the slide 232 translates in the longitudinal direction.

An actuator 238, such as a linear or other motor, is affixed to the rack 218 and the radiation source 112. The actuator 238 is magnetically actuated via a magnetic plate 240 affixed to the inner side 204 of the frame portion 202 and residing between the inner side 204 and the actuator 238. The slide 224 is affixed to the collimator 114. A counter balance mass 242, which is discussed in greater detail below, is affixed to the rack 220 of the first bearing and the slide 232 of the third bearing. As a result, the radiation source/collimator 112/114 translate together with the rack 218 and slide 224 in one direction and the counter balance mass 242 translates with the rack 220 and the slide 232 in the opposing direction, relative to the frame portion 202, along the longitudinal direction.

A position measurement device 244, such as an encoder or the like, is coupled to the actuator 238, the slide 224 and/or the source/collimator 112/114, and determines an absolute and/or relative position of the radiation source/collimator 112/114 relative to the frame portion 202. A moveable cable arm 246 is used to route any cables, connectors, and/or the like to the source 112 and/or the collimator 114. The cable arm 246 is flexible, which allows it to flex as needed as the source/collimator 112/114 move. A support structure may optionally be used to facilitate supporting the frame portions 202, the source/collimator 112/114, the actuator 238, and/or other components.

The source positioning systems 116 together move the source/collimator 112/114 along the longitudinal direction, which moves, via the first bearings 212, the counter balance masses 242, in an opposite direction along the longitudinal direction. Using counter balances masses as such may reduce forces on the rotating gantry 106, relative to a system in which the counter balance masses 242 are omitted. The actuator 238 is configured to move the source/collimator 112/114 through a common center of gravity 248. Each counter balance mass 242 is configured to move, relative to the source/collimator 112/114, so that the common center of gravity 248 does not change. The bearing 230 is placed in a center of gravity 250 of the counter balance mass 242, and the rack 220 is placed in line with the bearing 230 and the center of gravity 250. As such, the load on the bearing 230 is minimized.

Figure 4:
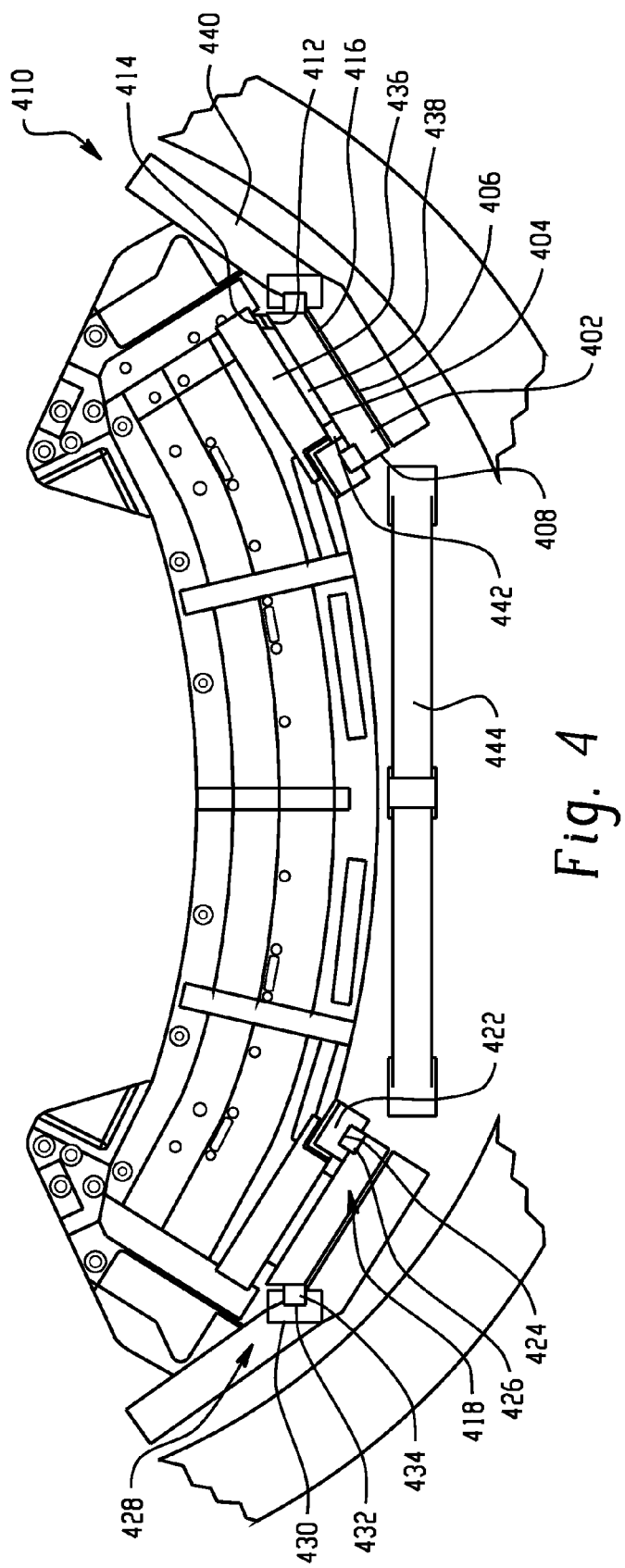
FIG. 4 illustrates an example detector array positioning system.

FIG. 4 illustrates an example detector array positioning system 122, which is similar to the source array positioning system 116 discussed herein. The detector array positioning system 122 includes an elongate frame portion 402, which is positioned under the detector array 120 such that the detector array 120 lies between the elongate frame portion 402 and the examination region 108. Alternatively, the frame portion 402 can be placed next to the ends of the detector array 120. The frame portion 402 includes a first major or inner side 404 facing the detector array 120, a second opposing major or outer side 406 facing away from the detector array 120, a first end (not visible) fastened to the rotating gantry 106 through a fastening mechanism as discussed above, and a second end 408, which may or may not be fastened to a structural support. Similar to the frame portion 202, the frame portion 402 may be part of the rotating gantry 106 in another embodiment.

The detector array positioning system 122 further includes a first bearing 410 affixed to the frame portion 402. The first bearing 410 is a rack and pinion type bearing like the first bearing 212, and includes a pinion 412 and racks 414 and 416. The racks 414 and 416 are located on opposite sides of the frame portion 402, with the rack 414 being next to the first inner side 404 and the rack 416 being next to the outer side 406. The gears 412-416 are arranged with respect to each other such that movement of any one of the gears 412-416 causes the other of the gears 412-416 to move, as discussed in connection with the source positioning system 116. The bearing 410 is affixed to the frame 402 so that the racks 414 and 416 translate in opposite directions back and forth along the longitudinal direction.

Second and third bearings 418 and 428 are similar to the bearings 220 and 230. The second bearing 418 includes a slide 422 with a groove 424 and a rail 426 affixed to the inner side 404, extending a substantial length of the frame portion 402, and disposed in the groove 424 such that the slide 422 is generally free to slide or translates along the rail 426. A third bearing 428 includes a slide 430 with a groove 432 and a rail 434 affixed to the inner side 404, extending a substantial length of the frame portion 402, and disposed in the groove 432 such that the slide 430 is generally free to slide or translates along the rail 434. The bearings 418 and 428 are affixed to the frame and configured so that the slides 422 and 430 translate in a direction of the longitudinal axis 110.

An actuator 436, such as a linear or other motor, is affixed to the rack 414 and the detector array 120. The actuator 436 is magnetically actuated via a magnetic plate 438 affixed to the first side 404 of the frame portion 402 and resides between the frame portion 402 and the actuator 436. The slide 422 is also affixed to the detector array 120. A counter balance mass 440 is affixed to the track 414 and the second slide 430. As a result, the detector array 120 translates with the rack 416 and slide 422 in one direction and the counter balance mass 440 translates with the rack 416 and the slide 430 in the opposing direction, relative to the frame portion 402. A position measurement device 442, such as an encoder or the like, determines an absolute or relative position of the detector array 120 relative to the frame portion 402. A moveable cable arm 444 is used to route any cables, connectors, and/or the like to the detector array 120.

The detector positioning systems 122 move the detector array 120 along the longitudinal direction, which moves, via the first bearing 410, the counter balance mass 440, in an opposite direction along the longitudinal direction. This may reduce forces on the rotating gantry 106, relative to a system in which the counter balance 440 is omitted. By placing the actuator 436 below the detector array 120, the actuator attraction force may help the detector array 120 withstand centrifugal forces.

Variations are contemplated.

For explanatory purposes, the above with described in relation to a configuration in which the source 112 and the collimator 114 moved together. However, in another embodiment, the source 112 may tilt independent of the collimator 114. In such an instance, both the source 112 and the collimator 114 may tilt together or the source 112 may tilt will the collimator 114 remains stationary relative to the source 112.

It is to be appreciated that the counter balance masses 242 and 440 can be actuated upon directly such as with a linear motor on the counterbalance. In one instance, this further reduces supporting frame forces and gear loads.

In another embodiment, the counter balance masses 242 and 440 are omitted.

In another embodiment, the detector positioning system 122 is omitted. In this embodiment, the source/collimator 112/114 may still move as discussed herein via the source positioning system 116.

Figure 5:
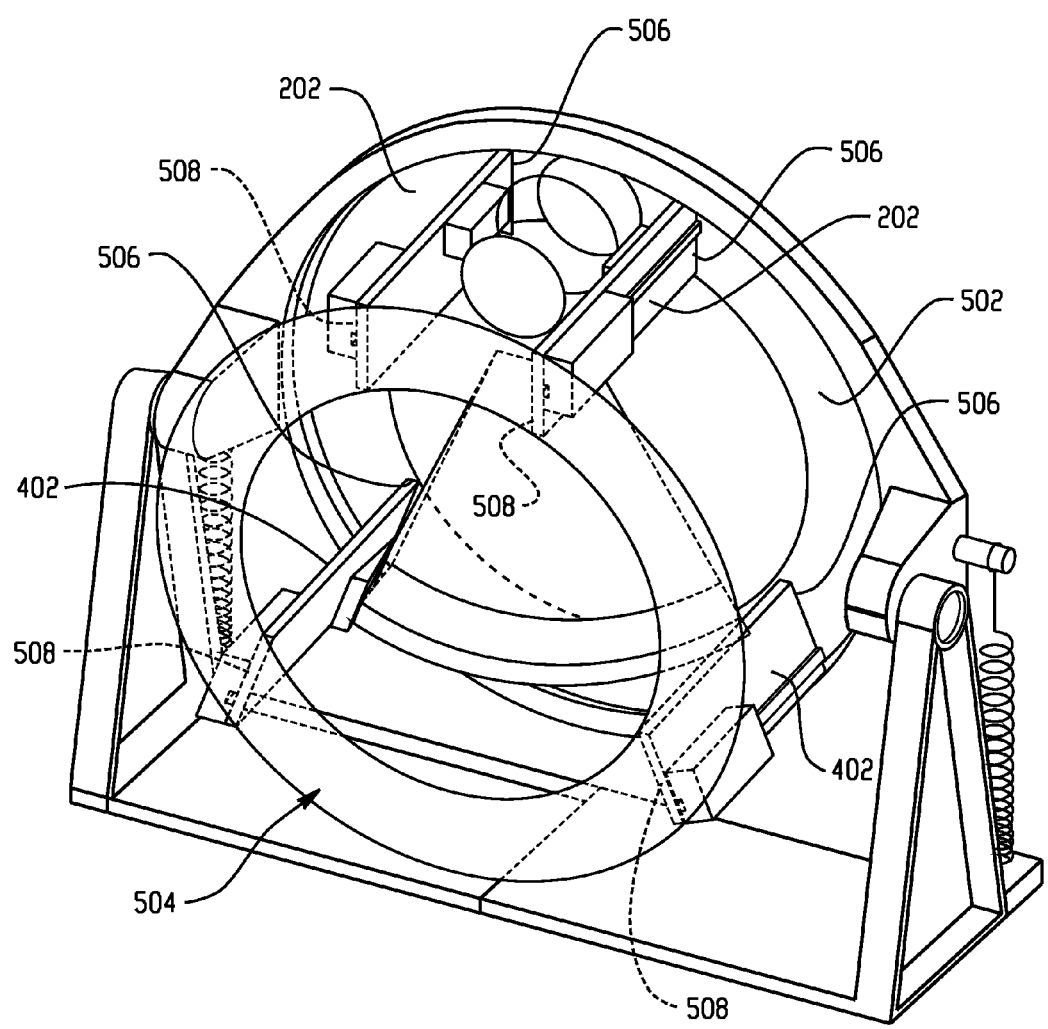
FIG. 5 illustrates an example in which the imaging system includes a dual-plate rotor that supports the source/collimator and detector array positioning systems.

In the illustrated embodiment, one of the ends of the frames 202 and 402 of the positioning systems 116 and 122 are affixed to the rotating gantry 106. In another embodiment, the rotating gantry 106 includes a first or back plate, such as an annular plate 502, and a second or front plate, such as an annular plate 504, shown in FIG. 5. With this embodiment, ends 506 of the frame portions 202 and 402 are fastened to the back plate 502 and ends 508 of the frame portions 202 and 402 are fastened to the front plate 504. In another embodiment, the front plate may only extend from frame portion 202 to frame portion 202 and/or from frame portion 402 to frame portion 402, or some distance less than a complete circle. In yet another embodiment, the front plate may include one or more other shaped structural members. In still another embodiment, structural members may be affixed to the side 204, the side 206, a top, and/or a bottom of the frame portions 202.

In the illustrated example, the source/collimator 112/114 and the detector array 120 are independent and distinct subsystems that move under the control of different controllers 118 and 124. FIG. 6 illustrates an embodiment in which the source/collimator 112/114 and the detector array 120 are physically coupled together by a structural coupling 602. First ends 604 of the coupling 602 are physically coupled to the source 112 and/or the collimator 114. Second ends 606 are physically coupled to the detector array 120. In this example, the second ends 606 are part of a carriage 608, which runs along a bottom of the detector array 120. In addition, a single position controller 610 can be used to drive both the source and the detector array positioning systems 116 and 122.

In the above discussion, the positioning systems 116 and 122 translate the source/collimator 112/114 and the detector array 120. It is to be appreciated that in another embodiment that the source/collimator 112/114 and the detector array 120 can additionally or alternatively be configured to tilt with respect to the stationary gantry 102. This may be advantageous when scanning a desired region of anatomy while avoiding scanning another region of the anatomy. This is shown in connection with FIGS. 7a, 7b, 8a, 8b, 9a, and 9b, which show the rotational and translational relationship between the source/collimator 112/114 and the detector array 120 via three rotational positions when scanning the inner ear while avoiding irradiating the optic nerve. Of course, tilting the source/collimator 112/114 and the detector array 120 (with or without translating the source/collimator 112/114 and the detector array 120) can also be used to avoid irradiating other tissue.

FIG. 7a shows a side view of the scanner 100. In this example, the rotating gantry 106 is at an angle at which the source/collimator 112/114 are located at about twelve O'clock and the detector array 120 is located at about six O'clock. While moving to this angular position, the source/collimator 112/114 translates away from the patient in a direction of the longitudinal axis, and the detector array 120 translates toward the patient in a direction of the longitudinal axis. As such, at this angular position the radiation beam is directed from the source 112 to the detector array 120 at an acute angle such that the radiation beam avoids the optic nerve, but traverses the inner ear. FIG. 7b shows this view looking into the source 112 (which is part of an image system 710) in a direction towards the examination region 108. A positioning system 702 translates and rotates the source/collimator 112/114 and the detector array 120. As shown, the positioning system 702 includes actuators $704_1$ and $704_2$, such as pistons or other fluid actuators, that drive guide arms $706_1$ and $706_2$ pivotably connected to pivots $708_1$ and $708_2$ affixed to opposing sides of the image system 710, which collectively includes the source/collimator 112/114 and the detector array 120. In this example, the guide arms $706_1$ and $706_2$ are similarly actuated to translate the source/collimator 112/114.

In FIG. 8a, the rotating gantry 106 has rotated to an angle at which the source/collimator 112/114 are located at about three O'clock and the detector array 120 is located at about nine O'clock, and the radiation beam is directed into the page. At this angular position, the source/collimator 112/114 and the detector array 120 are aligned with each other along the transverse axis. In addition, the rotating gantry 106 is tilted, thereby tilting the source/collimator 112/114 and the detector array 120, causing the radiation beam to cut through the examination region at an angle such that the radiation beam irradiates the inner ear while avoiding the optic nerve. FIG. 8*b* shows this view looking into the source 112, wherein the image system 710 is tilted by moving the guide arm 706$_2$ to a greater extent than the guide arm 706$_1$.

Figure 9B:
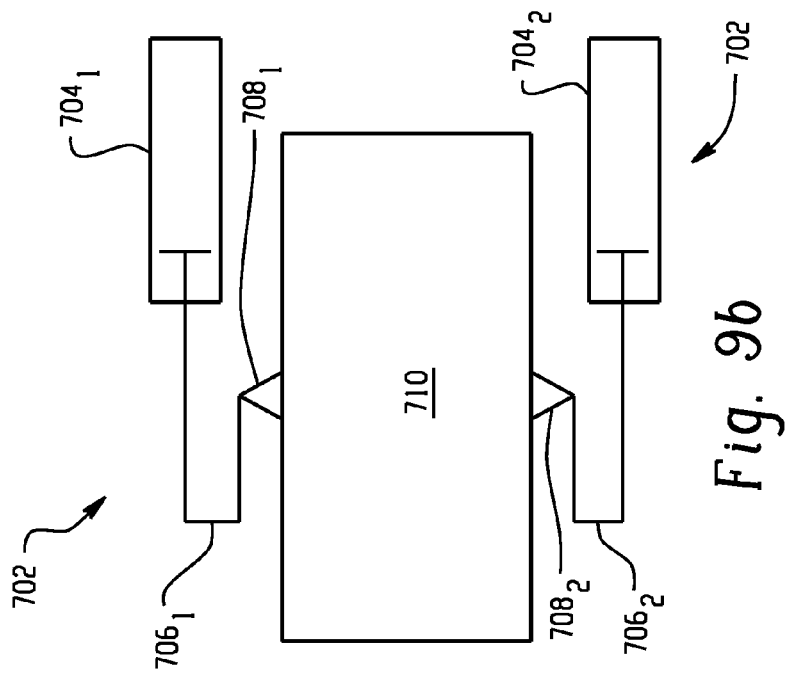
Figure 9A:
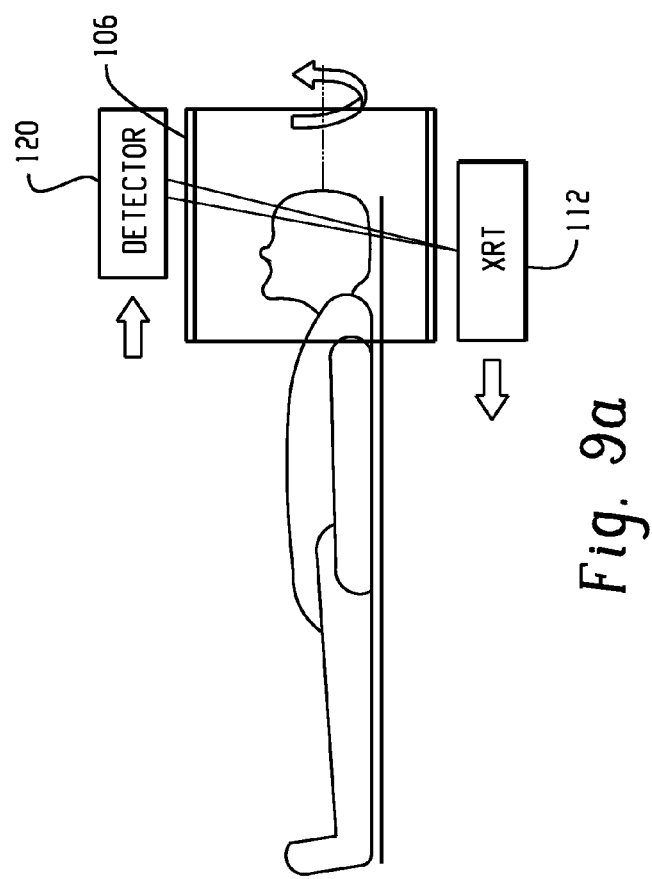

In FIG. 9*a*, the rotating gantry 106 has rotated such that the source/collimator 112/114 are located at about six O'clock and the detector array 120 is located at about twelve O'clock. While moving to this angular position, the source/collimator 112/114 translates towards the patient in a direction of the longitudinal axis, and the detector array 120 translates away from the patient in a direction of the longitudinal axis. As such, the radiation beam is directed from the source 112 to the detector array 120 at an angle such that the radiation beam avoids the optic nerve, but traverses the inner ear. FIG. 9*b* shows this view looking into source 112, wherein the guide arms 706$_1$ and 706$_2$ are again similarly actuated such that the image system 710 is not tilted.

It is to be understood that the above shows a snap shot at three different angular positions and that the motion can be continuous as the rotating gantry 106 rotates. Also note that rotary and linear actuators could replace the pivot and second linear actuator. Furthermore, the source/collimator 112/114 and the detector array 120 could be placed on linear bearings for axial freedom and then guided using a surface with bearings.

Figure 10:
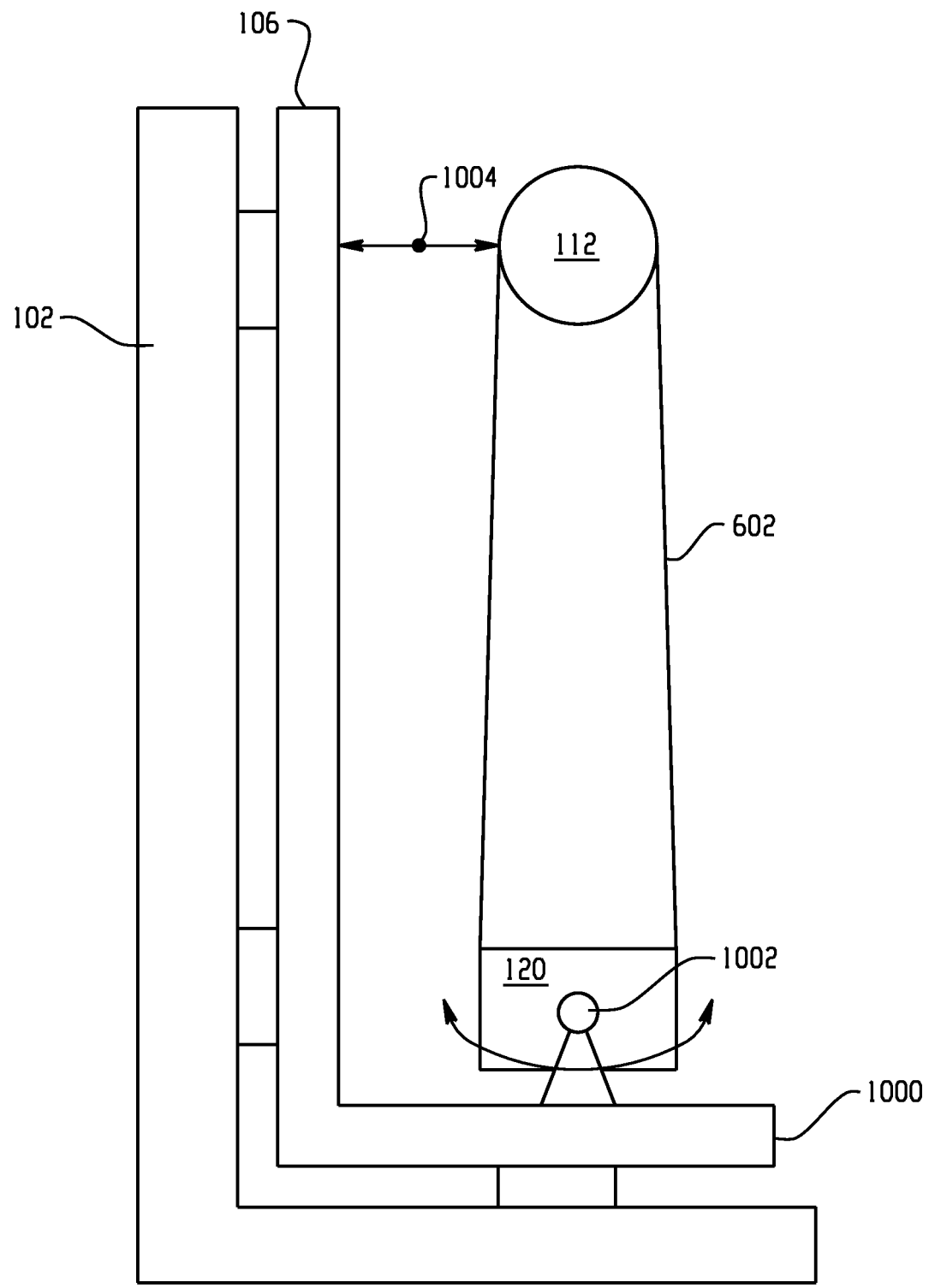
FIG. 10 illustrates an example in which the detector array is pivotably attached to the rotor.

In another embodiment, the detector array 120 is configured to pivot rather than translate or rotate as described above. This is shown in FIG. 10 in which the detector array 120 is pivotably attached to the rotating gantry 106. As shown, the source/collimator 112/114 and detector array 120 are coupled together via a coupling such as the coupling 602 discussed in connection with FIG. 6. The rotating gantry 106 includes a protrusion 1000, which extends from the rotating gantry 106 along an axis parallel to the longitudinal axis 110. A pivot 1002 is affixed to the protrusion 1000. The detector array 120 is pivotably attached to the pivot 1002. As the source/collimator 112/114 translate in a direction 1004 along the longitudinal axis as describe herein, the detector array 120 pivots about the pivot 1002. In another instance, the coupling 602 is omitted and separate drives are used to translate the source 112 and pivot the detector array 120.

In another embodiment, a tilted beam geometry is achieved electronically through translating the source/collimator 112/114 without tilting the source/collimator 112/114 and without tilting, pivoting or translating the detector array 120. As such, an elliptical trajectory at a desired tilt angle can be achieved by translating the source/collimator 112/114. In one instance, a tilt angle of ±30 degrees is achieved by translating the source/collimator 112/114 along the longitudinal axis over 40 centimeters (cm). This geometry is shown in connection with FIGS. 11 and 12.

Figure 11:
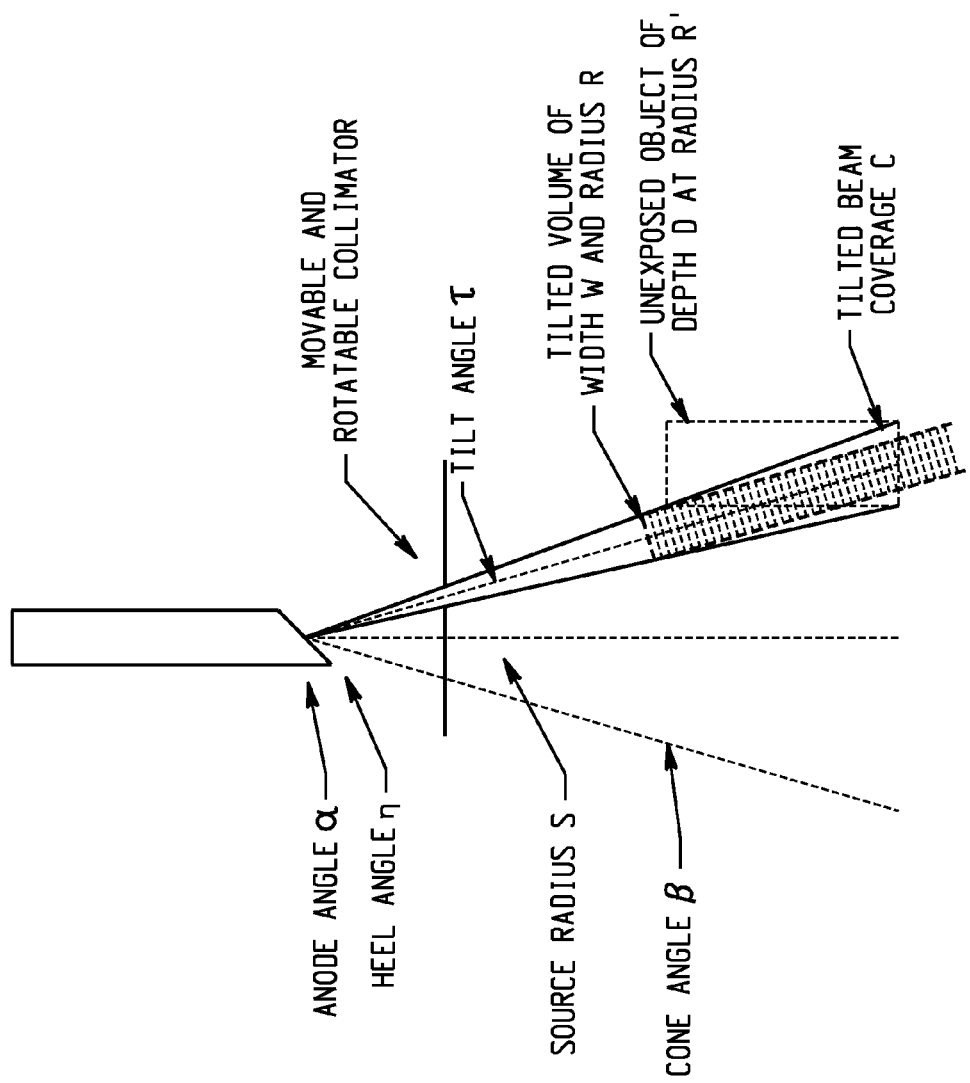
FIGS. 11 and 12 illustrate an example in which a tilt angle trajectory is achieved by translating the source and adjusting collimation width.

With respect to FIG. 11, assuming that a middle of a tilted beam with a tilt beam coverage of C is aligned vertically with an unexposed object of width D at a radius R' to be avoided (width C=D), then the following approximate equations describe the tilted beam geometry: $D \approx R' \cdot \beta = R' \cdot (\alpha - \eta) = C \approx W \cdot S/(S-R)$ and $\tau \approx \beta - (W/2)/(S-R)$, wherein D is the width of the unexposed object at the radius R', C is the beam coverage, $\beta$ is the cone angle, $\alpha$ is the anode angle, $\eta$ is the heel angel, W is the tilted volume width at radius R, S is the source radius, and $\tau$ is the tilt angle. For $\alpha=8°$, $\eta=4°$, R=12.5 cm, R'=10 cm, S=57 cm: $\beta=4°$, $D=C\approx0.7$ cm, $\tau\approx3.6°$, and $W\approx0.55$ cm, and for $\alpha=12°$, $\eta=4°$, R=12.5 cm, R'=10 cm, S=57 cm: $\beta=8°$, $D=C\approx1.4$ cm, $\tau\approx7.3°$, and $W\approx1.1$ cm.

Figure 12:
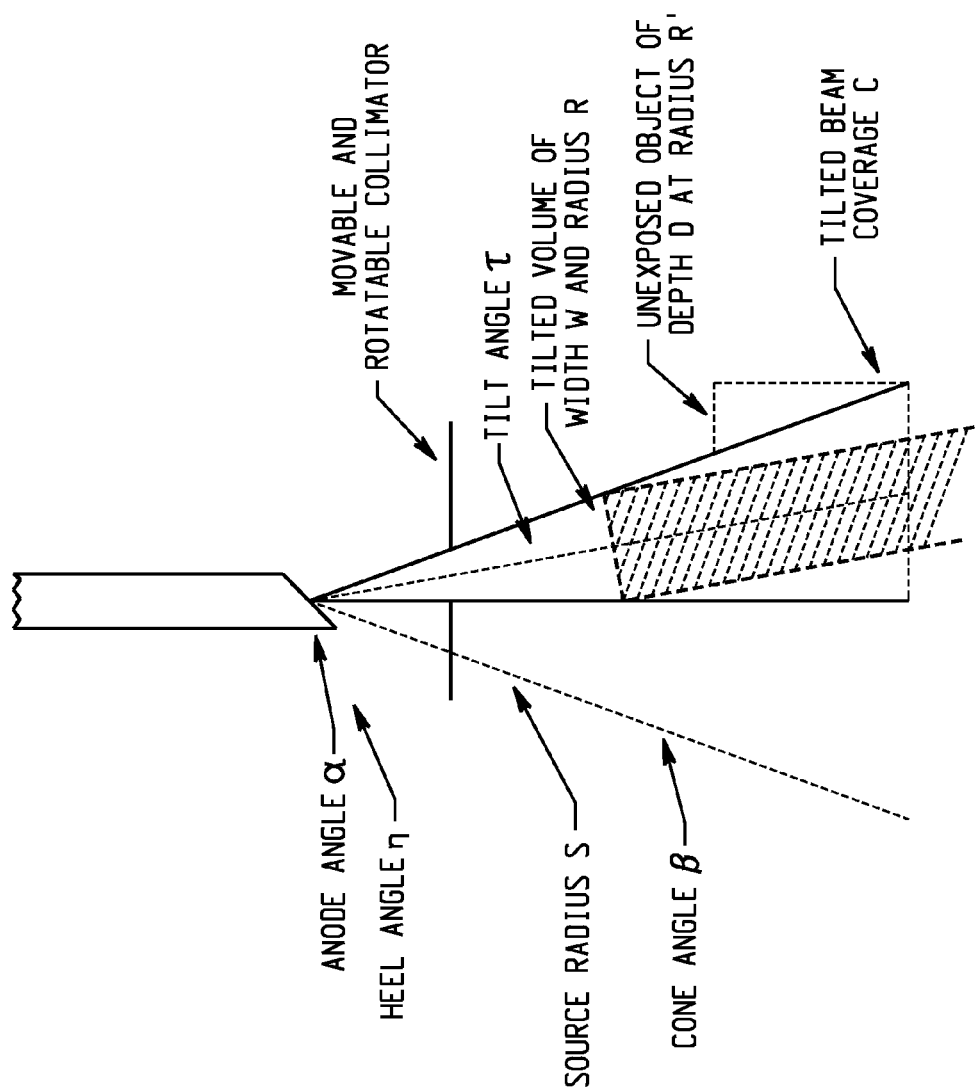

With respect to FIG. 12, assuming that a far edge of the tilted beam of width $C\approx\beta\cdot S$ is aligned vertically with the far edge of the unexposed object of width D, then the following approximate equations describe the tilted beam geometry: $D\approx R'\cdot\beta=R'\cdot(\alpha-\eta)$, $W\approx C\cdot(S-R)/S$ and $\tau\approx\beta/2$. For $\alpha=8°$, $\eta=4°$, R=12.5 cm, R'=10 cm, S=57 cm: $\beta=4°$, $C\approx4$ cm, $D\approx0.7$ cm, $\tau\approx2°$, and $W\approx3.1$ cm, and for $\alpha=12°$, $\eta=4°$, R=12.5 cm, R'=10 cm, S=57 cm: $\beta=8°$, $C\approx8$ cm, $D\approx1.4$ cm; $\tau\approx4°$, and $W\approx6.2$ cm.

Electronic tilt may become more useful for larger cone angles, in which case exposure of larger objects can be avoided (>1.4 cm for an anode angle of 12°). The detector need not be moved and a 2D anti-scatter grid can still be utilized. The collimator needs to be moved in the opposite direction of the source and rotated to keep the beam aligned with the tilted plane. If the source and detector are both tilted as they move in opposing directions, a much larger tilt angle can be achieved (e.g. 15.7 degrees for a source movement of 32 cm). However, the collimation must still rotate to keep the beam aligned with the tilted plane at 90°.

Figure 13:
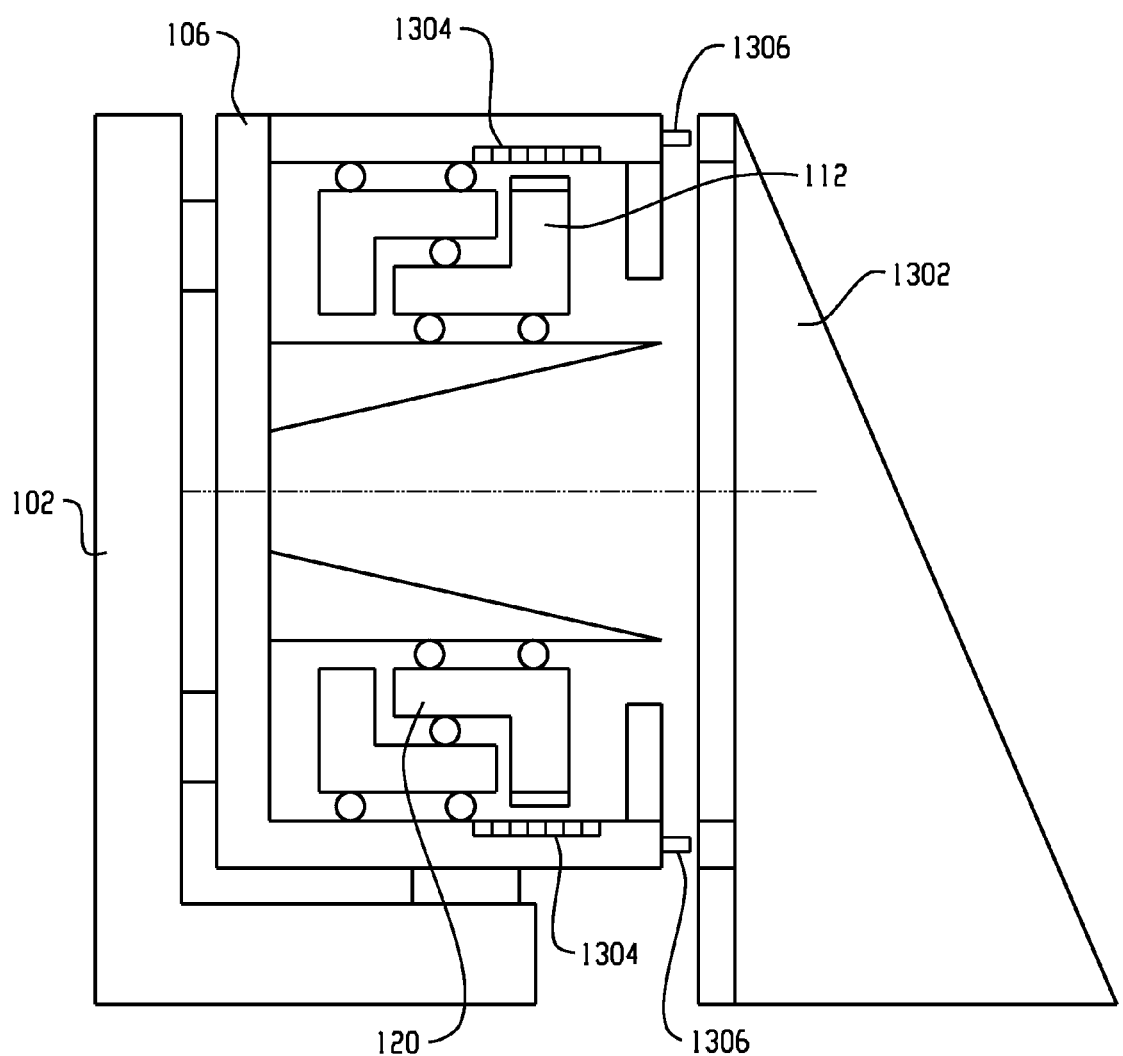
FIG. 13 illustrates an example wherein a separate reference frame is used to determine the position of the source/collimator and the detector array.

In the illustrated example, the rotating gantry 106 is used as reference for the position measurement system. As a result, various inaccuracies may be introduced into the measurement. For example, inaccuracy due to distortion of the rotor from vibrations of the rotor due to imbalance or reaction forces, mechanical stresses due to e.g. gravity or centrifugal forces, or the limited accuracy of the rotational motion of the rotor (stacked degrees of freedom) may be introduced. In the embodiment illustrated in FIG. 13, the scanner 100 includes a separate reference frame, or a metrology frame 1302, which is isolated from, but close to the rotating gantry 106 of the scanner 100. In this embodiment, the total measurement loop consists of two sensors per stage: a set of first or local sensors 1304 that measures the displacement of source 112 and the detector array 120 relative to the rotating gantry 106, and a second or reference sensor 1306 that measures the displacement of the rotating gantry 106 relative to the metrology frame 1302. In one instance, the set of sensors 1304 includes a cluster of three sensors placed on a circle at different angles. For in-machine calibration, one of the reference sensors needs to be replaced by a cluster of three reference sensors placed on a circle at different angles (with specific spacing).

As described herein, the x-ray tube 112, the source collimator 114, and/or the detector array 120 translate along the z-axis and/or tilt in a direction of the z-axis independent of and/or with each other and/or the stationary gantry/frame. It is to be appreciated that each of these components may move independent of and/or in coordination with one or more of the other components. As such, in one instance the source 112 and the detector 120 translate and the collimator blades move in coordination to create an effective tilt without having to tilt the stationary gantry 102. In another instance, the source 112 is capable of a large cone angle with the source 112 and collimator 114 translating in an opposite direction as the detector array 120 create an effective tilt without having to tilt the stationary gantry 102. In this instance, a one-dimensional anti-scatter grid can be used. The collimator 114 may also tilt with the source 112. By suitably tilting the detector array 120, a two-dimensional anti-scatter grid can be used.

Figure 14:
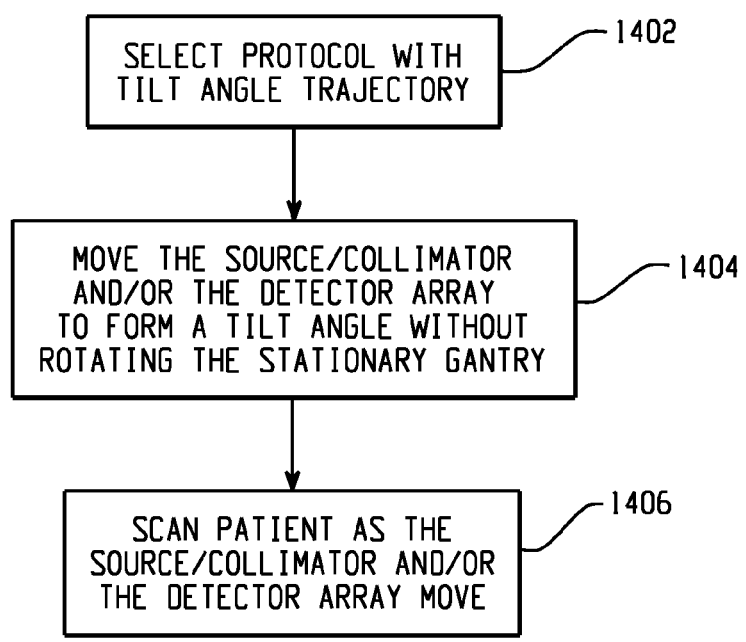
FIG. 14 illustrates a method.

In another instance, the source 112 tilts and translates, the collimator 114 translates along with the source 112, and the detector array 120 translates in an opposite direction to create an effective tilt without having to tilt the stationary gantry 102. In this instance, a one-dimensional anti-scatter grid can be used. By suitably tilting the detector array 120, a two-dimensional anti-scatter grid can be used. The collimator 114 may also tilt with the source 112. In another instance, the source 112, the collimator 114, and the detector array 120 all tilt in coordination on a common frame along a central axis to create an effective tilt without having to tilt the stationary gantry 102. In this instance, a two-dimensional anti-scatter grid can be used. Other combinations of movement of the source 112, the collimator 114, and/or the detector array 120 are also contemplated. Operation is discussed in connection with FIG. 14. It is to be understood that the ordering of the following acts is for explanatory purposes and not limiting.

At 1402, a scan protocol including a tilt angle trajectory is selected.

At 1404, the source/collimator 112/114 and/or the detector array 120 translate and/or rotate along the longitudinal axis without tilting the stationary gantry 102 as described herein.

Concurrently, at 1406, a scan is performed.

Figure 15:
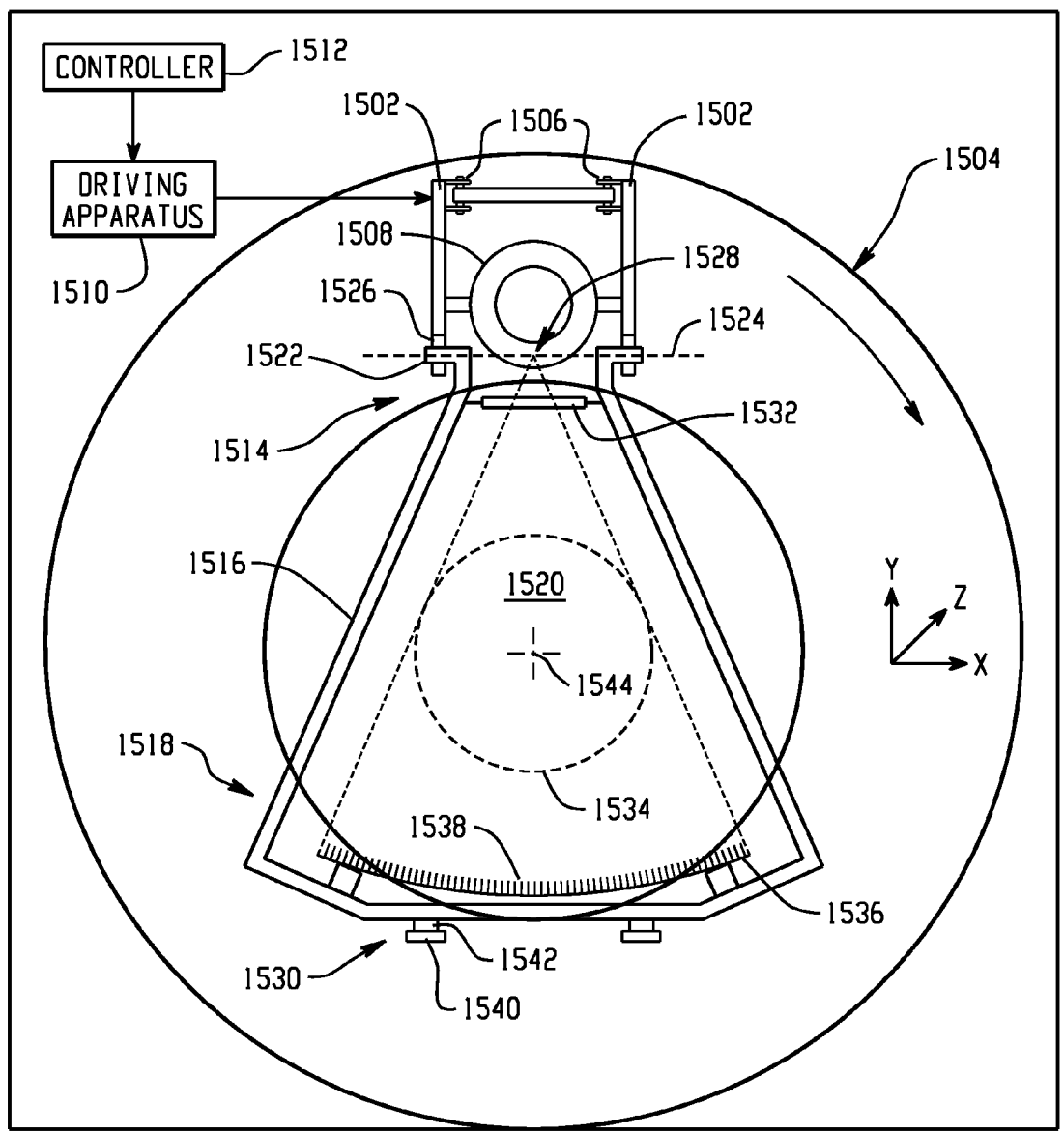
Figure 16:
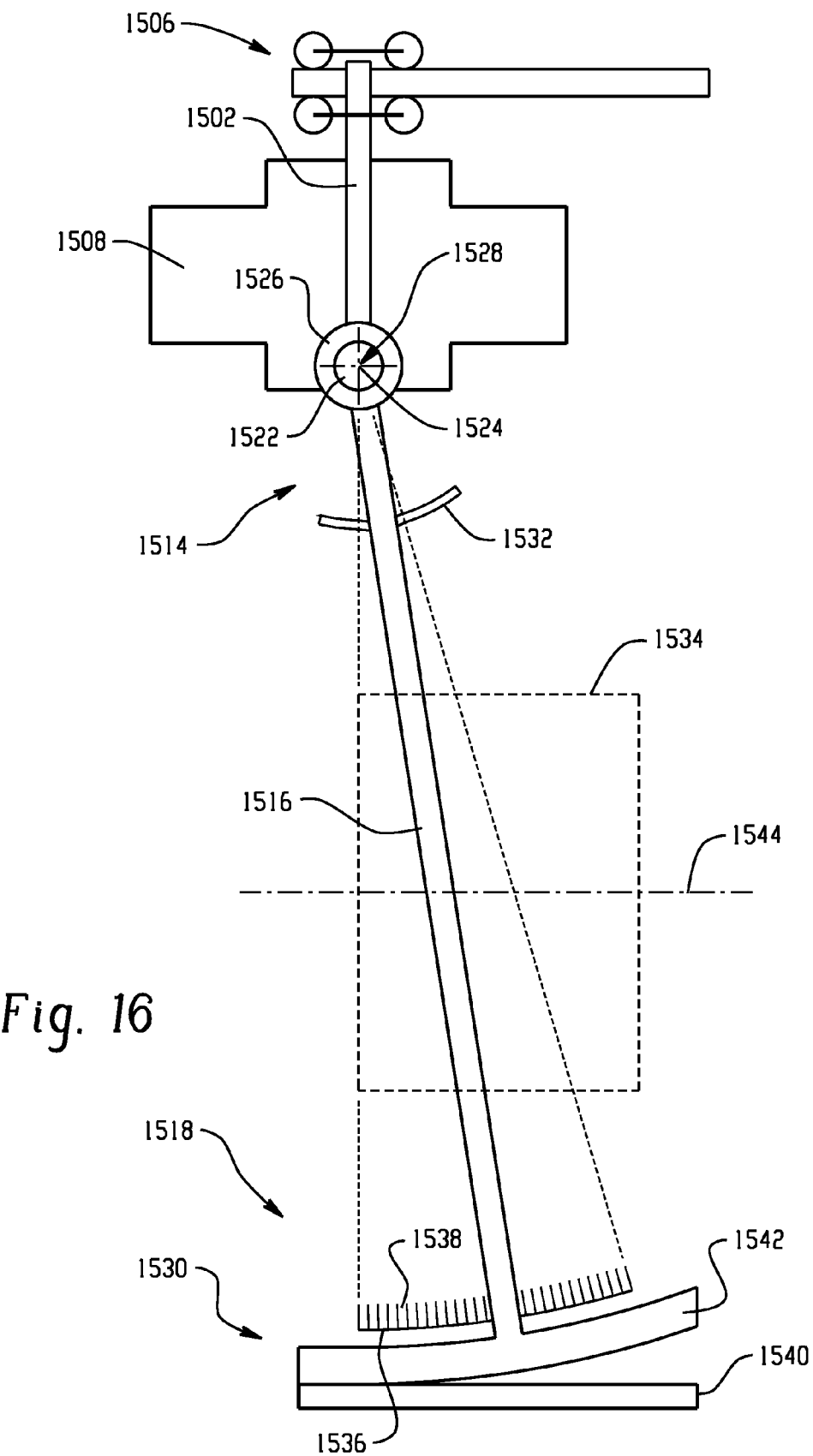

Turning to FIGS. 15 and 16, a radiation source carriage 1502 is moveably affixed to a rotating gantry 1504 via one or more bearings 1506, which may include linear slide, ball, and/or other bearings such as those discussed above as well as other bearings. The radiation source carriage 1502 translates via the bearings 1506 along the axis of rotation 1544 in the z-direction. A radiation source 1508 is affixed to and translates with the radiation source carriage 1502. A source carriage driving apparatus 1510 drives the radiation source carriage 1502 in the z-direction. The driving apparatus 1510 may include a motor or the like that drives a lead screw, a ball screw, a chain, a spear gear, a belt, or like, which drives the radiation source carriage 1502. A controller 1512 controls the driving apparatus 1510 based on a scan protocol or otherwise.

A mechanical joint or frame 1516 couples the radiation source 1508 and a detector array 1536. A first end 1514 of the frame 1516 is pivotably affixed to the radiation source 1508. In the illustrated embodiment, the radiation source 1508 includes two couplings 1526, and the first end 1514 of the frame 1516 includes two pivots 1522 that extend through the couplings 1526. The two pivots 1522 are configured to pivot about an imaginary pivot axis 1524, which extends through center regions of the couplings 1526, is parallel to the x axis and perpendicular to the z-axis, and intersects a focal spot 1528 of the radiation source 1508. In other embodiments, the system may include less or more pivots 1522 and/or couplings 1526.

A second end 1518 of the frame 1516 is moveably affixed to the rotating gantry 1504, across from the radiation source 1508, on an opposite side of an examination region 1520. The second end 1518 of the frame 1516 is affixed to the rotating frame 1504 via bearings. First portions 1540 of the bearings 1530 are affixed to the rotating gantry 1504 and extend in the z-direction. The illustrated location of the first portions 1540, under the detector array 1536, is provided for explanatory purposes and can be elsewhere located, for example, on the sides of the detector array 1536 or above the detector array 1536, outside of the field of view 1534. In addition, in other embodiments the system may include less or more bearings 1530.

Second portions 1542 of the bearings 1530 are affixed to or part of the second end 1518 of the frame 1516, and are located on the frame 1516 in accordance with the location of the first portions 1540 on the rotating gantry 1504. As shown in FIG. 16, the second portions 1542 are arc-shaped and can roll (or rock) on the first portions 1540 of the bearings 1530. As the frame 1516 is coupled to the radiation source 1508, the second portions 1542 roll in coordination with translational movement of the source carriage 1502 along the axis rotation 1544. In one instance, at least one the portions 1540 and 1542 includes a toothed gear or rim that engages a complementary portion of the other of the portions 1540 and 1542. The complementary portion may also include teeth with valleys therebetween or alternatively recesses which accept the teeth of the toothed gear.

The detector array 1536, which is located across from the radiation source 1508 on an opposing side of the examination region 1520, is affixed to the second end 1518 of the frame 1516. The detector array 1536 includes at least one detector pixel that detects radiation traversing the examination region 1520 and generates a signal indicative of detected radiation. An anti-scatter grid 1538 attenuates and substantially prevents scatter radiation from striking the detector array 1536. The anti-scatter grid 1538 may be a one or a two dimensional anti-scatter grid. The anti-scatter grid 1538 may also be omitted.

A source collimator 1532, which collimates, along the z-axis, radiation emitted by the radiation source 1508, is affixed to the frame 1516 between the radiation source 1508 and a field of view 1534. One or more counter weights (not shown for purposes of clarity), such as those described herein, can be used to counter the shifting masses of the source carriage 1502, the radiation source 1508, the frame 1516, the collimator 1532, the detector 1536 and/or one or more other moving components.

Operation is discussed in connection with FIGS. 17-19. In FIG. 17, the source carriage 1502 is located at a generally central position 1702 of travel. At this position, the frame 1516 extends from the radiation source 1508 along an imaginary line 1704, which is perpendicular to a central region of the axis of rotation 1544. The collimator 1532 is located at a position in which an aperture thereof is generally symmetric about the imaginary line 1704, a central region 1706 of the second portion 1542 of the bearing 1530 rests on the first portion 1540 of the bearing and aligns with imaginary line 1704, and a central region 1708 of the detector array 1536 is focused at the focal spot 1528.

In FIG. 18, the source carriage 1502 is located at one end 1802 of travel. As the source carriage 1502 translates to this position, the radiation source 1508 translates along with it. The pivots 1522 of the frame 1516 pivot about the pivot axes 1524 and the second portions 1542 of the bearings 1530 roll on the first portions 1540 in coordination with the translation, and the frame 1516 extends from the focal spot 1528 at an angle, with respect to the imaginary line 1704, which increases in magnitude from about zero to about $\alpha$. The collimator 1532 also translates, and the central region 1708 of the detector array 1536 remains focused at the focal spot 1528.

In FIG. 19, the source carriage 1502 is located at another end 1902 of travel. As the source carriage 1502 translates to this position, the pivots 1522 pivot about the pivot axis 1524 and the second portions 1542 of the bearings 1530 roll in an opposite direction relative to FIG. 18. Similarly, the frame 1516 extends from the focal spot 1528 at an angle, with respect to the imaginary line 1704, which increases in magnitude from about zero to about $\alpha$. Again, the collimator 1532 also translates, and the central region 1708 of the detector array 1536 remains focused at the focal spot 1528.

In another embodiment, the frame 1516 is omitted, and a detector carriage driving apparatus drives or rolls a detector carriage, which holds the detector array 1536, in a manner similar to the rolling of the second portion 1542 of the bearing and in coordination with the source carriage driving apparatus 1510.

Figure 20:
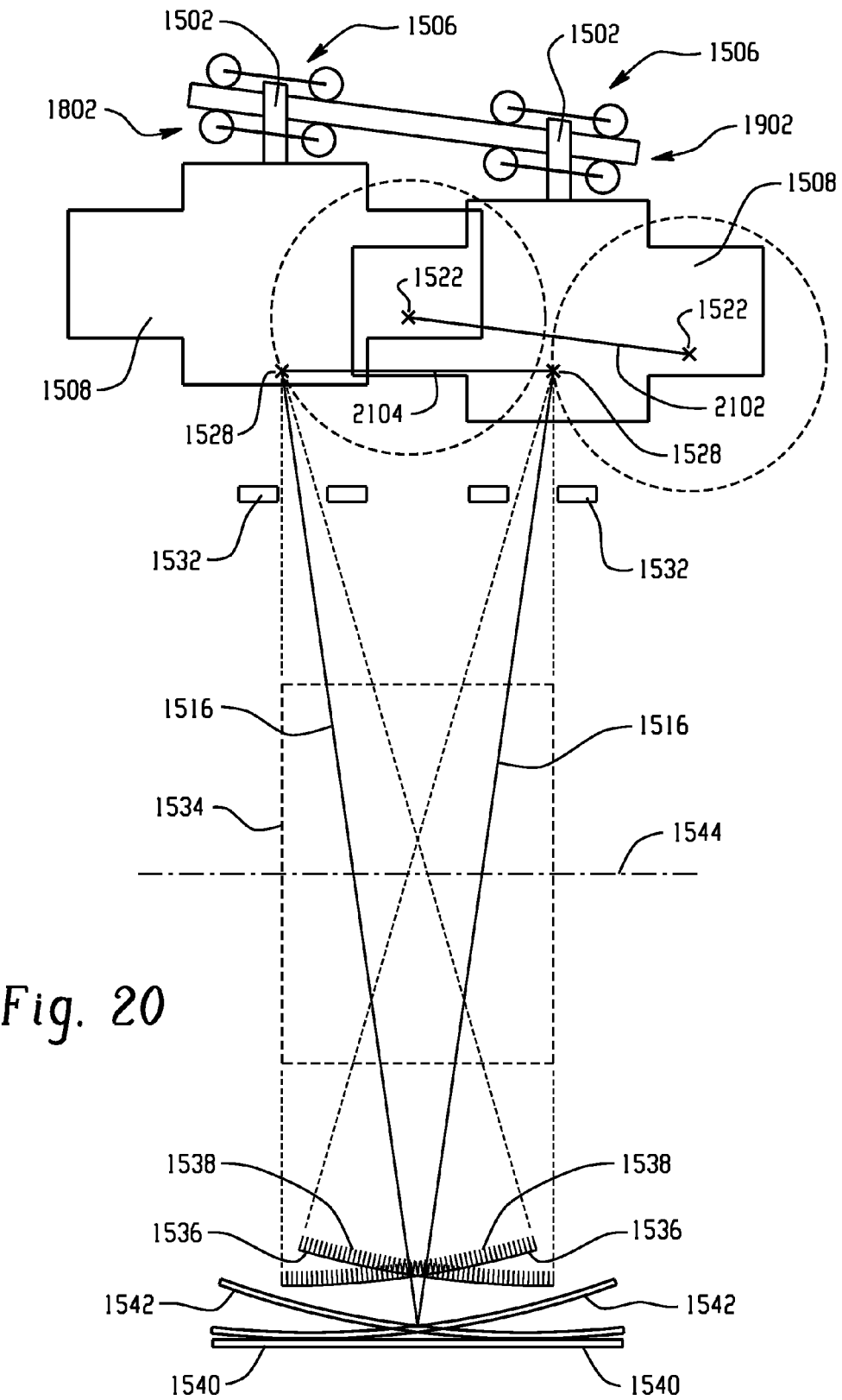
FIGS. 20 and 21 illustrate an embodiment in which the anode includes a curved surface.
Figure 21:
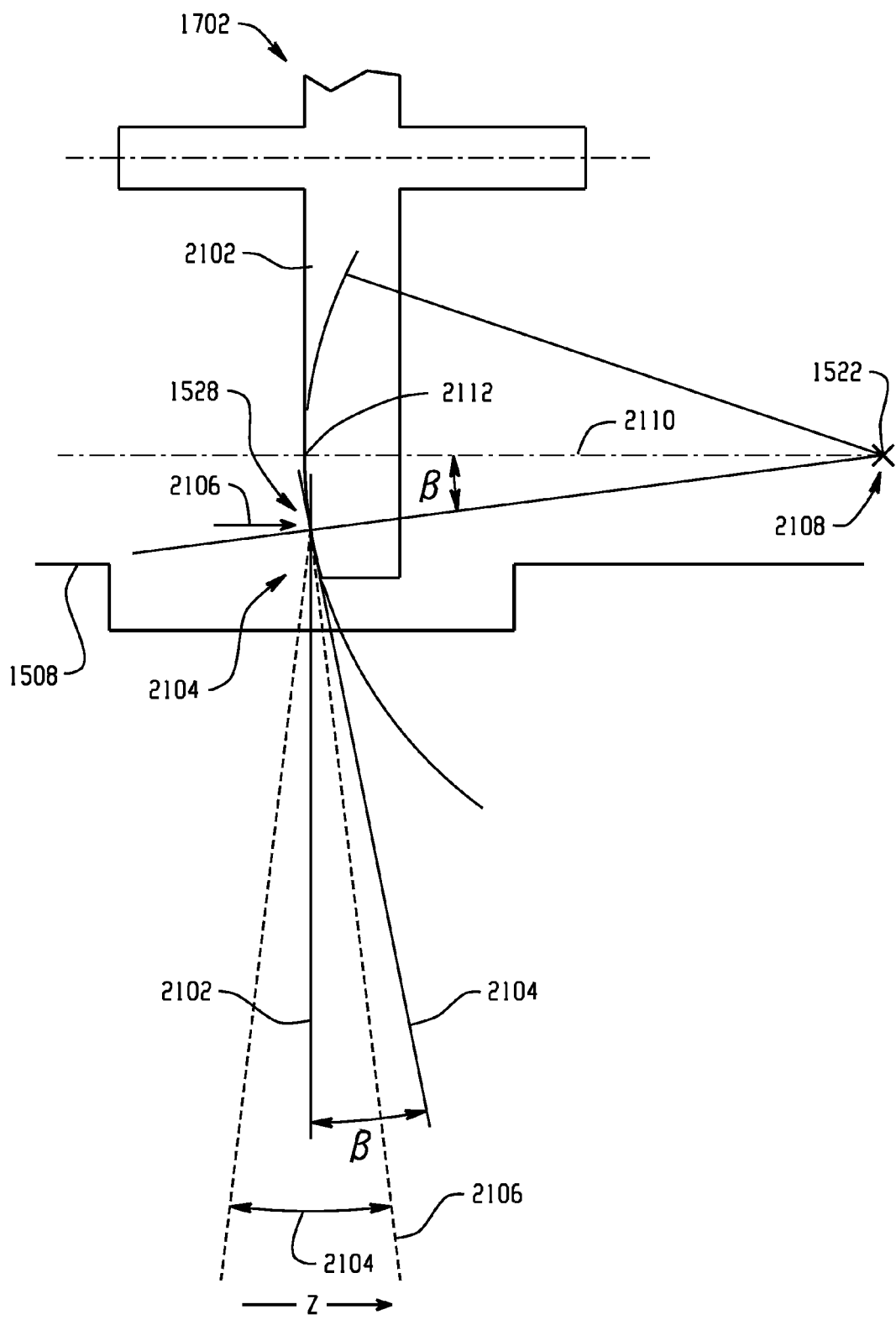

FIGS. 20 and 21 depict a variation of the embodiment of FIGS. 15-19. In this variation, the source carriage 1502 translates at an incline/decline.

FIG. 20 shows a superposition of the source carriage 1502 at the two end positions 1802 and 1902. As with FIGS. 17-19, when the source carriage 1502 is located at a central position of travel, the frame 1516 extends along the imaginary line perpendicular to the central region of the axis of rotation 1544, the collimator 1532 is located at a position in which an aperture thereof is generally symmetric about the imaginary line, the central region of the second portion 1542 of the bearing 1530 rests on the first portion 1540 of the bearing and aligns with the imaginary line, and the central region of the detector array 1536 is focused at the focal spot 1528.

As the source carriage 1502 translates to the positions 1802 and 1902, the radiation source 1508 translates along the incline and decline, the pivots 1522 pivot about the pivot axes 1524 and the second portions 1542 roll in coordination with the translation, the frame 1516 extends from the focal spot 1528 at an angle with respect to the imaginary line, the collimator 1532 translates, and the central region of the detector array 1536 remains focused at the focal spot 1528.

Such an embodiment is well-suited for use with a rotating anode type radiation source having a variable anode angle, which is the angle between the radiation beam and the anode surface, as the incline and decline translational movement of the radiation source 1508 can be used to compensate for any change in the location of the focal spot 1528 within the x-ray source in order to keep the distance between a moving focal spot 1528 and the axis of rotation 1544 constant, as the source carriage 1502 translates. Such a radiation source may be used to provide a smaller anode angle, increased resolution, and increased maximum power, relative to a configuration in which the anode angle is not variable. FIG. 21 illustrates an example radiation anode 2102 with a variable anode angle.

In FIG. 21, the cross section of the rotating anode 2102 has a curved portion 2104 such as a generally convex shape with a suitable radius of curvature such as on the order of one (1) to twenty (20) centimeters (cm). An electron beam 2106 is directed (e.g., electrostatically or electromagnetically) at a location on the anode 2102 that corresponds to a focus position of the detector array 1536, thereby generating the focal spot 1528 at the location that corresponds to the focus position of the detector array 1536. In FIG. 21, the radiation source 1508 is located at the central position 1702 of travel, the detector array 1536 is centered below the radiation source 1508, and a range 2107 of a cone beam 2106 is about symmetrical with respect to a center line extending from the focal spot 1528 perpendicularly to the detector array 1536. At other positions of travel, the electron beam 2106 is directed at (alternatively) higher or lower locations on the anode 2102, and still corresponding to the focus position of the detector array 1536, thereby generating the focal spot 1528 at the other locations.

The pivot 1522 of the frame 1516 is pivotably affixed to the radiation source 1508 at a location 2108, which is offset from the focal spot 1528 and coincides with a midpoint of the curvature as shown by an imaginary line 2110. Consequently, the distance between the focal spot 1528 and the location 2108 coincides with or is about equal to the radius of curvature. A distance between the focal spot 1528 and the point 2112 defines an angle β, which is the effective anode angle, or the angle between an imaginary line 2102 extending vertically from the focal spot 1528 and an imaginary line 2109 extending tangentially at the anode surface through the focal spot 1528. This angle represents the mean take-off-angle of the cone beam and corresponds to the anode angle for a cone-shaped anode surface.

Returning to FIG. 20, as the carriage 1502 translates along the incline and decline 2103, the radiation source 1508 translates along the incline and decline 2103 and the electron beam 2106 is re-focused on the anode 2102 and the focal spot 1528 translates along a line 2111, which is parallel to the axis of rotation 1544. Thus, in one instance the translation of the radiation source 1508 along the incline and decline can be used to compensate for any change in the distance between the moving focal spot 1528 and the axis of rotation 1544, as the source carriage 1502 translates. This may provide for a focal spot 1528 and an effective anode angle β that remains substantially constant for all or some sub-set of radiation source positions, if desired.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

The invention is claimed to be:

1. A medical imaging system, comprising:
 a generally stationary gantry;
 a rotating gantry, rotatably supported by the generally stationary gantry, that rotates about a longitudinal axis around an examination region;
 a radiation source that emits a radiation beam that traverses the examination region, wherein the radiation source is moveably affixed to the rotating gantry so as to translate in a direction of the longitudinal axis with respect to the rotating gantry while scanning a subject in the examination region;
 a detector array that detects the radiation beam that traverses the examination region and generates a signal indicative thereof, wherein the detector array is moveably affixed to the rotating gantry so as to move in coordination with the radiation source while scanning the subject in the examination region; and
 a counter balance mass moveably affixed to
 1) the rotating gantry so as to translate in a direction of the longitudinal axis with respect to the rotating gantry, wherein the counter balance mass and the radiation source concurrently move in opposite directions, or
 2) the detector array so as to translate in a direction of the longitudinal axis with respect to the rotating gantry, wherein the counter balance mass and the detector array concurrently move in opposite directions.

2. The medical imaging system of claim 1, wherein the radiation source translates in the direction of the longitudinal axis during a scan such that the radiation beam traverses through the examination region at a tilt angle without having to tilt the generally stationary gantry.

3. The medical imaging system of claim 1, wherein the radiation source translates in the direction of the longitudinal axis during a scan, thereby moving the radiation beam along an elliptical trajectory without having to tilt the generally stationary gantry.

4. The medical imaging system of claim 1, wherein the detector array translates in a same direction as the radiation source, and further including a two-dimensional anti-scatter grid disposed between the examination region and the detector array.

5. The medical imaging system of claim 1, further including:
a radiation source positioning system that moveably couples the radiation source to the rotating gantry, the radiation source positioning system comprising:
an elongate structural component affixed to the rotating gantry and extending along the longitudinal direction;
an actuator attached the radiation source; and
a first bearing including a first translating portion and a non-translating portion, wherein the first bearing is disposed between the elongate structural component and the actuator, and the first translating portion is affixed to the radiation source and the non-sliding portion is affixed to the elongate structural component;
wherein the actuator translates the first translating portion with respect to the non-translating portion, thereby moving the radiation source in the longitudinal direction.

6. The medical imaging system of claim 5, further including a magnetic plate that magnetically actuates the actuator, wherein the magnetic plate resides between the elongate structure component and the actuator.

7. The medical imaging system of claim 6, wherein the first bearing further includes a second translating portion attached to a counter balance mass, and moving the first translating portion in one direction moves the second translating portion in an opposing direction, thereby moving the radiation source and the counter balance mass in opposing directions.

8. The medical imaging system of claim 1, further including a position measurement device that determines a position of the radiation source with respect to the rotating gantry.

9. The medical imaging system of claim 1, wherein at least one of the radiation source or the detector array tilt relative to the stationary gantry.

10. The medical imaging system of claim 1, wherein the radiation source and the detector array translate in opposite directions along the longitudinal axis.

11. The medical imaging system of claim 1, further including a source position controller and a detector array position controller, wherein the source position controller controls the position of the radiation source and the detector array position controller controls the position of the detector array, and the radiation source and the detector array independently translate in along the longitudinal axis.

12. The medical imaging system of claim 1, further including a mechanical coupling that physically couples the radiation source and the detector array, wherein the radiation source and the detector array translate together along the longitudinal axis.

13. The medical imaging system of claim 12, further including a single position controller that controls the movement of both the radiation source and the detector array.

14. A medical imaging system, comprising:
a rotating gantry that rotates about a longitudinal axis around an examination region;
a radiation source that emits a radiation beam that traverses the examination region, wherein the radiation source is moveably affixed to the rotating gantry so as to translate in a direction of the longitudinal axis with respect to the rotating gantry while scanning a subject in the examination region; and
a detector array that detects the radiation beam that traverses the examination region and generates a signal indicative thereof, wherein the detector array is moveably affixed to the rotating gantry so as to move in coordination with the radiation source while scanning the subject in the examination region; and
wherein the rotating gantry tilts in the direction of the longitudinal axis, thereby tilting the radiation source and the detector array in the direction of the longitudinal axis.

15. The medical imaging system of claim 14, wherein the radiation source and the detector array concurrently translate and tilt in the direction of the longitudinal axis as the rotating gantry rotates about the examination region.

16. A medical imaging system, comprising:
a rotating gantry that rotates about a longitudinal axis around an examination region;
a radiation source that emits a radiation beam that traverses the examination region, wherein the radiation source is moveably affixed to the rotating gantry so as to translate in a direction of the longitudinal axis with respect to the rotating gantry while scanning a subject in the examination region;
a detector array that detects the radiation beam that traverses the examination region and generates a signal indicative thereof, wherein the detector array is moveably affixed to the rotating gantry so as to move in coordination with the radiation source while scanning the subject in the examination region; and
the detector array is mechanically attached to the radiation source and pivotably attached to the rotating gantry, wherein translating the radiation source pivots the detector array about a pivot.

17. A medical imaging system, comprising:
a rotating gantry that rotates about a longitudinal axis around an examination region;
a radiation source that emits a radiation beam that traverses the examination region, wherein the radiation source is moveably affixed to the rotating gantry so as to translate in a direction of the longitudinal axis with respect to the rotating gantry while scanning a subject in the examination region;
a detector array that detects the radiation beam that traverses the examination region and generates a signal indicative thereof, wherein the detector array is moveably affixed to the rotating gantry so as to move in coordination with the radiation source while scanning the subject in the examination region;
a reference frame isolated from, but located close to the rotating gantry;
a first sensor that measures a displacement of the radiation source and the detector array relative to the rotating gantry; and
a second sensor that measures a displacement of the rotating gantry relative to the reference frame;
wherein a position of the radiation source and the detector array is determined based on measurements from the first and second sensors.

18. An imaging system, comprising:
a rotating gantry that rotates about a longitudinal axis around an examination region;
a radiation source with a focal spot that emits radiation that traverses the examination region, wherein the radiation source is moveably affixed to the rotating gantry and translates in a direction of the longitudinal axis; and
a detector array focused at the focal spot, wherein the detector array rolls in coordination with the translation of the radiation source, thereby maintaining the focus between the detector array and the focal spot.

19. The imaging system of claim 18, wherein the radiation source translates along an axis parallel to the longitudinal axis.

20. The imaging system of claim 18, wherein the radiation source translates along an axis that is inclined/declined with respect to the longitudinal axis.

21. The imaging system of claim 20, wherein the radiation source includes an anode and the focal spot corresponds to a location on the anode receiving an electron beam, wherein the location on the anode receiving the electron beam changes as a function of the radiation source position along the longitudinal axis.

22. The imaging system of claim 21, wherein a distance between the focal spot and the longitudinal axis is maintained as the radiation source translates along the longitudinal axis.

23. The imaging system of claims 18, further including a source carriage moveably affixed to the rotating gantry, wherein the radiation source is affixed to the source carriage and translates along the longitudinal axis as the source carriage translates along the longitudinal axis.

24. The imaging system of claim 23, further including a frame that couples the radiation source and the detector array, wherein the frame includes:
at least one pivot that is pivotably affixed to the radiation source; and
at least one member moveably affixed to the rotating gantry so as to roll with respect to the rotating gantry, wherein the least one pivot pivots and the curved member rolls in coordination with translation of the radiation source along the longitudinal axis.

25. The imaging system of claim 24, wherein the detector array is affixed to and rolls with the member, which is arc-shaped.

26. The imaging system of any of claims 18, wherein the radiation source includes an anode with a variable anode angle.

27. The imaging system of claims 18, wherein the radiation source is an rotating anode type x-ray source which includes an anode having a convex cross-sectional shape.

28. A computed tomography (CT) scanner, comprising:
a stationary gantry;
a rotating gantry that rotates about a longitudinal axis around an examination region;
a radiation source that emits a radiation beam; and
a detector array that detects the radiation beam that traverses the examination region and generates a signal indicative thereof;
wherein the radiation source and the detector array translate along the longitudinal axis in coordination to create an effective tilt without tilting the stationary gantry and the radiation source tilts relative to the stationary gantry and translates, and the detector array translates in an opposite direction.

29. The CT scanner of claim 28, further comprising:
an anti-scatter grid disposed between the examination region and the detector array, wherein the anti-scatter grid is a two-dimensional anti-scatter grid.

30. The CT scanner of claim 28, wherein the radiation source and the detector array translate in opposite directions.

31. The CT scanner of claim 28, wherein the detector array tilts relative to the scanner.

32. The CT scanner of claim 31, further comprising:
a source collimator with a least one moveable radiation collimating plate that collimates the radiation beam emitted by the radiation source to produce a radiation beam that traverses the examination region, wherein the source collimator tilts with the radiation source.

33. The CT scanner of claim 31, further comprising:
a source collimator with a least one moveable radiation collimating plate that collimates the radiation beam emitted by the radiation source to produce a radiation beam that traverses the examination region, wherein the radiation source, the source collimator, and the detector array all tilt in coordination on a common frame along a central axis.

34. A method, comprising:
rotating a rotating gantry rotatably coupled to a stationary gantry about a longitudinal axis around an examination region;
translating a radiation source and a detector array, which are coupled to and rotate with the rotating gantry, in a direction of the longitudinal axis with respect to the stationary gantry during scanning; and
translating at least one counter balance mass while translating at least one of the radiation source and the detector array.

35. The method of claim 34, wherein translating the radiation source and the detector array causes a radiation beam to traverse the examination region at an acute angle with respect to a plane perpendicular to the longitudinal axis.

36. The method of claim 34, further including translating the radiation source and the detector array to form an elliptical radiation beam trajectory without tilting the stationary gantry.

37. The method of claim 34, further including tilting the detector array relative to the stationary gantry during scanning.

38. The method of claim 34, further including tilting the radiation source relative to the stationary gantry during scanning.

39. The method of claim 34, further including tilting the radiation source and the detector array in the direction of the longitudinal axis with respect to the stationary gantry during scanning.

40. A method, comprising:
translating a focal spot of a radiation source in a direction of a z-axis; and
concurrently rolling a detector array focused at the focal spot in coordination with the translating of the focal spot so as to maintain a focus between the detector array and the focal spot as the focal spot translates.

41. The method of claim 40, further including translating the focal spot along a path that is parallel to the z-axis.

42. The method of claims 40, further including translating the radiation source along a path that is inclined/declined relative to the z-axis.

43. The method of claim 42, further including moving a position of the focal spot in a direction of the z-axis as the radiation source translates.

44. The method of claim 40, further including translating the focal spot and the radiation source along a path that is parallel to the z-axis.

* * * * *